(12) United States Patent
Tajima et al.

(10) Patent No.: US 9,861,334 B2
(45) Date of Patent: Jan. 9, 2018

(54) RADIOGRAPHIC IMAGING SYSTEM, RADIOGRAPHIC IMAGING DEVICE, HANDHELD TERMINAL DEVICE AND RADIOGRAPHIC IMAGING METHOD

(71) Applicant: FUJIFILM CORPORATION, Minato-ku, Tokyo (JP)

(72) Inventors: Takashi Tajima, Kanagawa (JP); Haruyasu Nakatsugawa, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 215 days.

(21) Appl. No.: 14/811,839

(22) Filed: Jul. 29, 2015

(65) Prior Publication Data

US 2016/0029991 A1    Feb. 4, 2016

(30) Foreign Application Priority Data

Jul. 31, 2014  (JP) ................................ 2014-156939
Feb. 13, 2015  (JP) ................................ 2015-026944

(51) Int. Cl.
*A61B 6/00*      (2006.01)

(52) U.S. Cl.
CPC .......... *A61B 6/5294* (2013.01); *A61B 6/4266* (2013.01); *A61B 6/461* (2013.01);
(Continued)

(58) Field of Classification Search
CPC ..... A61B 6/542; A61B 6/4233; A61B 6/4405; A61B 6/461; A61B 6/54; A61B 6/4266;
(Continued)

(56) References Cited

U.S. PATENT DOCUMENTS

2011/0306882 A1*  12/2011  Hannon ............... A61B 6/4494
                                                     600/443
2012/0128127 A1*   5/2012  Chicchetti ................. G01T 7/00
                                                       378/62

(Continued)

FOREIGN PATENT DOCUMENTS

JP          2005-301492 A     10/2005

*Primary Examiner* — Hoon Song
(74) *Attorney, Agent, or Firm* — SOLARIS Intellectual Property Group, PLLC

(57) ABSTRACT

The present invention provides a radiographic imaging system, a radiographic imaging device, a handheld terminal device and a radiographic imaging method that may improve convenience for a user, in a case in which handheld terminal device is used for radiographic imaging. In a case where a radiographic image is imaged without using a console, the radiographic imaging device generates an image ID and transmits to the handheld terminal device. The handheld terminal device associates the received image ID with a patient ID and memorizes in a memory section. Meanwhile, the radiographic imaging device associates image data of the imaged radiographic image with the image ID and memorizes in a memory section. After imaging is completed, the console separately receives the associated image ID and patient ID from the handheld terminal device and receives the associated image ID and image data from the radiographic imaging device.

22 Claims, 27 Drawing Sheets

(52) U.S. Cl.
CPC .............. *A61B 6/464* (2013.01); *A61B 6/467* (2013.01); *A61B 6/468* (2013.01); *A61B 6/488* (2013.01); *A61B 6/54* (2013.01); *A61B 6/542* (2013.01); *A61B 6/548* (2013.01); *A61B 6/4494* (2013.01); *A61B 6/545* (2013.01); *A61B 6/563* (2013.01)

(58) Field of Classification Search
CPC ..... A61B 6/4429; A61B 6/465; A61B 6/5211; A61B 6/40; A61B 6/42; A61B 6/469; A61B 6/4014; G01N 2223/301; G01N 2223/308
See application file for complete search history.

(56) References Cited

U.S. PATENT DOCUMENTS

| | | | |
|---|---|---|---|
| 2014/0275954 A1* | 9/2014 | Ohta | A61B 6/465 600/407 |
| 2014/0276056 A1* | 9/2014 | Ohta | A61B 90/00 600/440 |

* cited by examiner

FIG.4

| IMAGING DEVICE ID | PATIENT ID | IMAGE ID |
|---|---|---|
| A | 001 | 1 |
| A | 002 | 2 |
| A | 003 | 3 |

FIG.6

| IMAGE ID | IMAGE DATA |
|---|---|
| 1 | x x x |
| 2 | x x x |
| 3 | x x x |

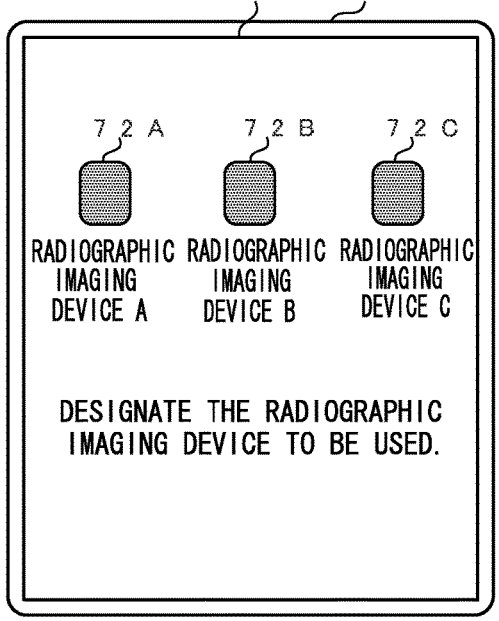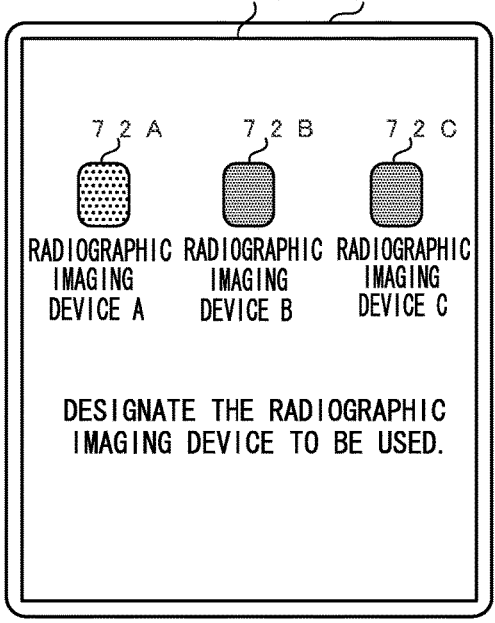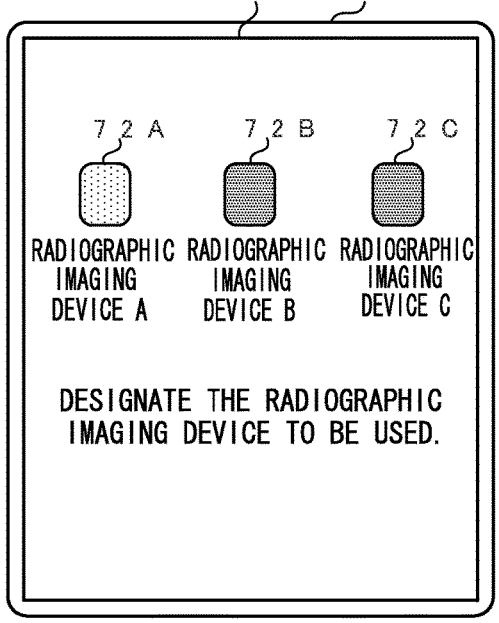

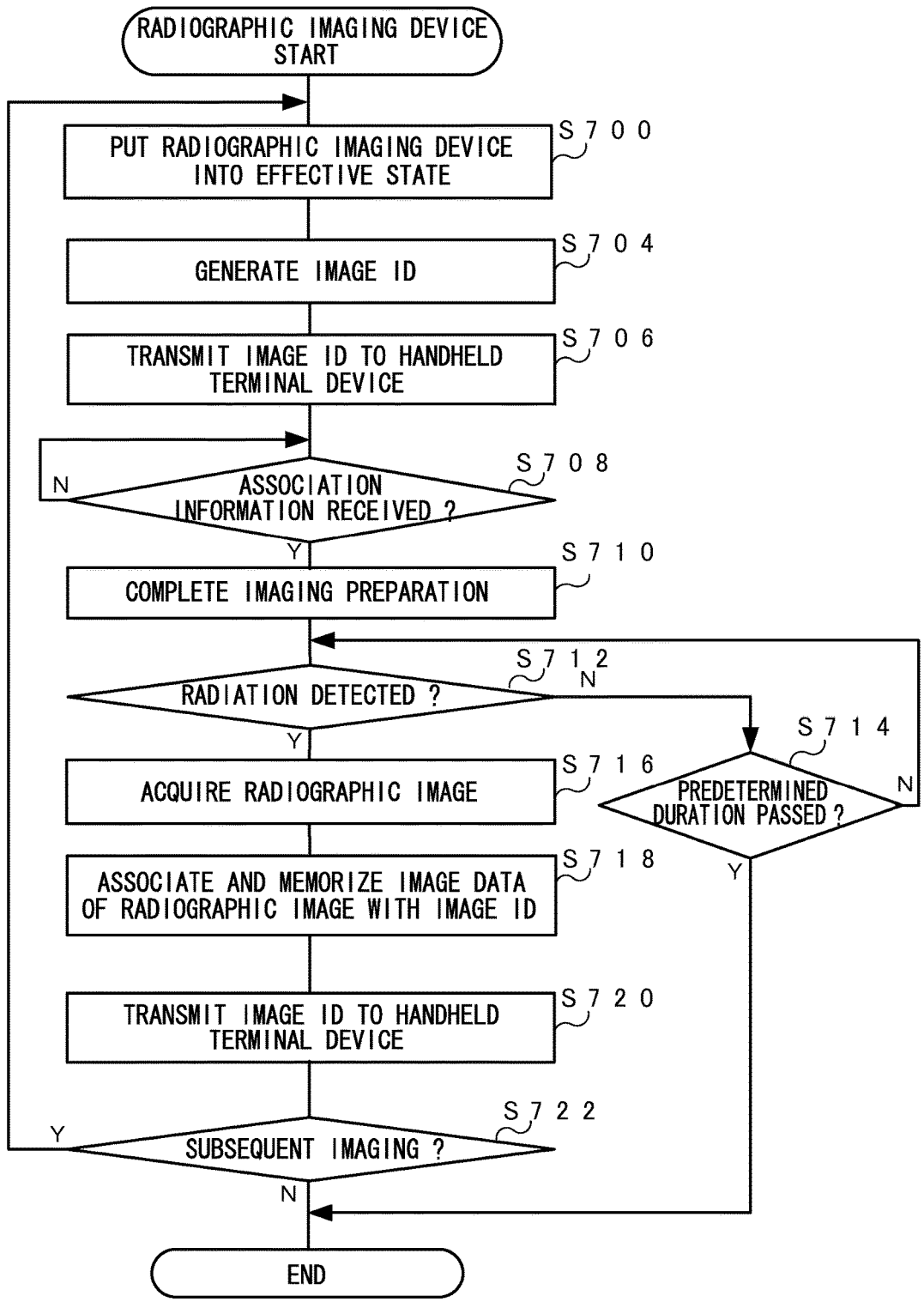

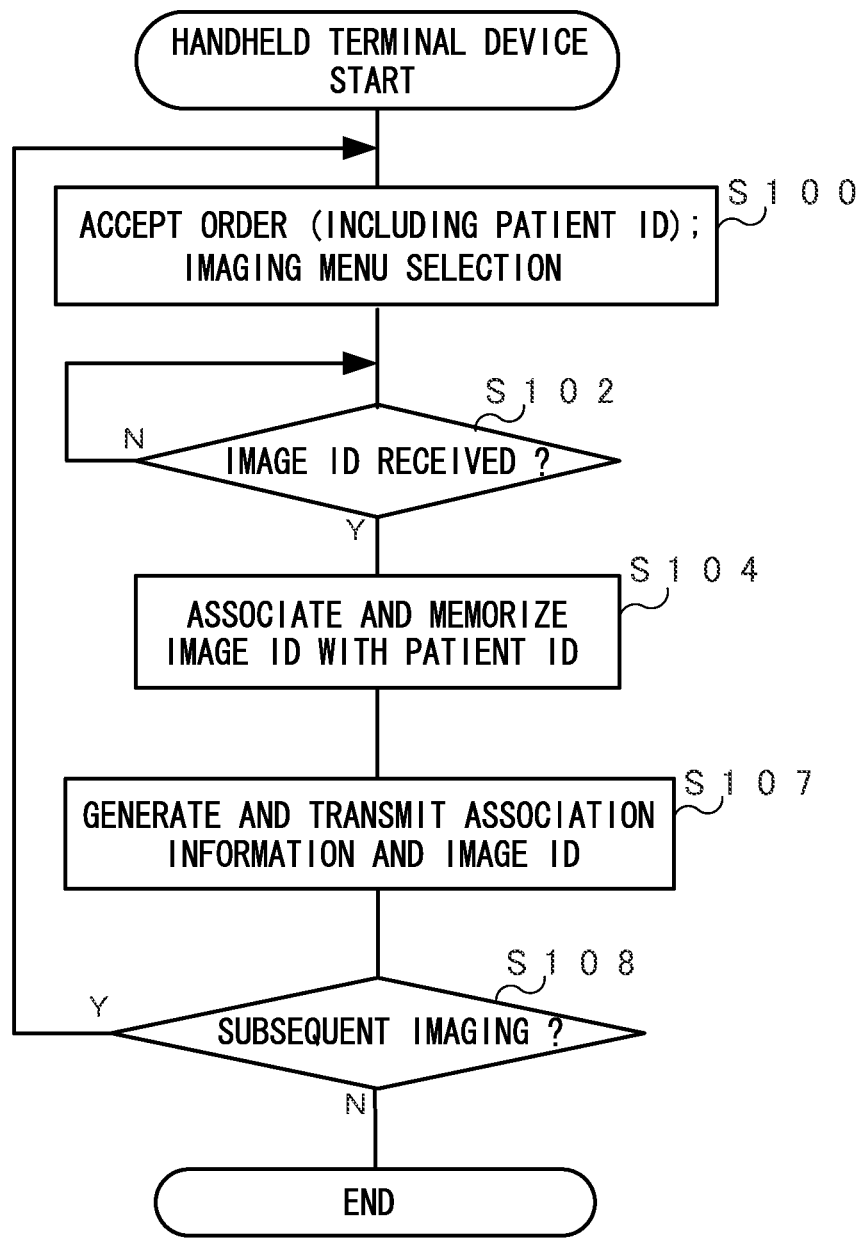

RADIOGRAPHIC IMAGING SYSTEM, RADIOGRAPHIC IMAGING DEVICE, HANDHELD TERMINAL DEVICE AND RADIOGRAPHIC IMAGING METHOD

CROSS-REFERENCE TO RELATED APPLICATIONS

This application claims priority under 35 USC 119 from Japanese Patent Application No. 2014-156939 filed on Jul. 31, 2014 and Japanese Patent Application No. 2015-026944 filed on Feb. 13, 2015, the disclosures of which are incorporated by reference herein.

BACKGROUND OF THE INVENTION

Field of the Invention

The present invention relates to a radiographic imaging system, a radiographic imaging device, a handheld terminal device and a radiographic imaging method.

Description of the Related Art

In recent years, handheld terminal devices such as personal digital assistants (PDAs) have been used in a case in which radiographic images are being imaged, because handheld terminal devices are easier to use than large devices, consoles and the like. For example, the technology recited in Japanese Patent Application Laid-Open (JP-A) No. 2005-301492 is known as a technology with which imaging of a radiographic image is performed using a PDA.

In a case in which radiographic images are imaged using a PDA, the PDA may be limited in functions, operations and the like compared to a console. Therefore, there is scope for improvement in regard to user convenience and suchlike for radiographers and the like.

SUMMARY OF THE INVENTION

The present invention provides a radiographic imaging system, a radiographic imaging device, a handheld terminal device and a radiographic imaging method that may improve convenience for a user in a case of using the handheld terminal device to image a radiographic image.

A first aspect of the invention is a radiographic imaging system including: a radiographic imaging device that images a radiographic image of an imaging target; a handheld terminal device; a first memory section at which image information of the radiographic image and identification information that identifies the image information are associated and memorized; and a second memory section, different from the first memory section, at which imaging target information relating to the imaging target and the identification information are associated and memorized, wherein the identification information identifying the image information is generated at one of the radiographic imaging device or the handheld terminal device, wherein the radiographic imaging device associates the identification information with the image information, and memorizes the same at the first memory section, wherein, in a case in which the imaging target information and the identification information have been associated and memorized at the second memory section, the handheld terminal device generates association information and transmits the association information to outside the handheld terminal device, and wherein the radiographic imaging device receives the association information transmitted from the handheld terminal device.

In a second aspect of the present invention, in the above aspect, the radiographic imaging device may include: the first memory section; an imaging section that images the radiographic image; a first generation section that generates the identification information; a first control section that controls to associate the image information with the identification information generated by the first generation section, and memorize the same at the first memory section; a first transmission section that transmits the identification information to the handheld terminal device; and a first reception section that receives the association information from the handheld terminal device, and the handheld terminal device may include: the second memory section; a second reception section that receives the identification information from the radiographic imaging device; an acquisition section that acquires the imaging target information; a second control section that controls to associate the imaging target information acquired by the acquisition section with the identification information received by the second reception section, and memorize the same at the second memory section; a second generation section that generates the association information in a case in which the imaging target information and the identification information have been associated and memorized by the second control section; and a second transmission section that transmits the association information generated by the second generation section to the radiographic imaging device.

In a third aspect of the present invention, in the above aspects, the handheld terminal device may permit imaging of the radiographic image at the radiographic imaging device in a case in which the association information has been generated.

In a fourth aspect of the present invention, in the above second aspect, the radiographic imaging device may generate the identification information with the first generation section, and may transmit the identification information by the first transmission section before imaging of the radiographic image by the imaging section; and after the transmission of the identification information, the first control section may permit the imaging of the radiographic image at the imaging section in a case in which the first reception section has received the association information.

In a fifth aspect of the present invention, in the above second aspect, the radiographic imaging device may transmit the identification information with the first transmission section after imaging of the radiographic image by the imaging section; and after the transmission of the identification information, the first control section may permit imaging of a subsequent radiographic image at the imaging section in a case in which the first reception section has received the association information.

In a sixth aspect of the present invention, in the above fifth aspect, the identification information that identifies the image information acquired by the imaging is generated by the first generation section after the imaging of the radiographic image by the imaging section.

In a seventh aspect of the present invention, in the above second to sixth aspects, the handheld terminal device may further include: an operation section at which a user performs an operation to enter the imaging target information; and a first acceptance section that, in a case in which the identification information has been received by the second reception section, accepts the imaging target information entered by the user with the operation section for the received identification information, and wherein the acquisition section may acquire the imaging target information accepted by the first acceptance section.

In an eighth aspect of the present invention, in the above second to seventh aspects, the handheld terminal device may further include a first display section that displays the identification information received by the second reception section; and the second control section may control to display the identification information received by the second reception section at the first display section.

In a ninth aspect of the present invention, in the above second to eighth aspects, the handheld terminal device may further include: a second display section that displays the imaging target information acquired by the acquisition section; and a second acceptance section that accepts an amendment performed by the user for the imaging target information displayed at the second display section, and wherein the second control section may control to display the imaging target information acquired by the acquisition section at the second display section, and may control to associate imaging target information that has been corrected in accordance with an amendment accepted by the second acceptance section with the identification information and to memorize the same at the second memory section.

In a tenth aspect of the present invention, in the above second to ninth aspects, a plurality of the radiographic imaging device may be provided; and the second control section of the handheld terminal device may control to associate the identification information transmitted by the first transmission section of the radiographic imaging device and received by the second reception section with information representing the radiographic imaging device that is the source of the transmission of the identification information, and to memorize the same at the second memory section.

In an eleventh aspect of the present invention, in the above second to tenth aspects, a plurality of the radiographic imaging device may be provided; the handheld terminal device may include a designation section at which at least one radiographic imaging device among the plurality of radiographic imaging devices is designated; and the second control section may control to associate information representing the radiographic imaging device that has been designated at the designation section with the identification information transmitted by the first transmission section of the radiographic imaging device and received by the second reception section, and to memorize the same at the second memory section.

In a twelfth aspect of the present invention, in the above eleventh aspect, if the second reception section receives the identification information from one of the radiographic imaging devices that is different from the radiographic imaging device designated by the designation section, the second control section of the handheld terminal device may control to associate information representing the radiographic imaging device that is the source of the transmission of the identification information with the identification information and to memorize the same at the second memory section.

In a thirteenth aspect of the present invention, in the above second to twelfth aspects, the first memory section may associate and memorize a plurality of the image information with a plurality of the identification information generated by the first generation section.

In a fourteenth aspect of the present invention, in the above second to thirteenth aspects, may further include a control device including: a third memory section at which the image information and imaging target information associated with the same identification information are associated and memorized; a third reception section that receives the image information and the corresponding identification information from the radiographic imaging device, and receives the imaging target information and the identification information associated with the imaging target information from the handheld terminal device; and a third control section that controls imaging of the radiographic image by the radiographic imaging device, and controls to associate the image information and the imaging target information associated with the same imaging identification information, and to memorize the same at the third memory section.

In a fifteenth aspect of the present invention, in the above second to fourteenth aspects, the handheld terminal device may further include a fourth control section that controls the imaging of the radiographic image by the radiographic imaging section.

In a sixteenth aspect of the present invention, in the above second to thirteenth aspects, the handheld terminal device may further include: a third memory section at which the image information and imaging target information associated with the same identification information are associated and memorized; a third reception section that receives the image information corresponding to the identification information received from the radiographic imaging device by the second reception section; and a third control section that controls imaging of the radiographic image by the radiographic imaging device, and controls to associate the image information and imaging target information associated with the same identification information, and to memorize the same at the third memory section.

In a seventeenth aspect of the present invention, in the above second to sixteenth aspects, the radiographic imaging device and the handheld terminal device communicate by at least one of wireless communications by electromagnetic waves and optical communications by light.

In an eighteenth aspect of the present invention, in the above second to seventeenth aspects, the radiographic imaging device may further include: a third generation section that generates a preview image from image data of the radiographic image; and a third transmission section that transmits image information of the preview image generated by the third generation section to the handheld terminal device, and the handheld terminal device may further include: a fourth reception section that receives the preview image from the radiographic imaging device; and a third display section that displays the preview image received by the fourth reception section.

In a nineteenth aspect of the present invention, in the above eighteenth aspect, the radiographic imaging device may further include a determination section that makes a determination as to whether the radiographic image imaged by the imaging section has been imaged on the basis of a false detection of radiation; and the third generation section may generate the preview image if the determination section determines that the radiographic image has been imaged on the basis of a false detection of radiation.

In a twentieth aspect of the present invention, in the above eighteenth aspect, the radiographic imaging device may further include a determination section that makes a determination as to whether the radiographic image imaged by the imaging section has been imaged on the basis of a false detection of radiation; and the third generation section may not generate the preview image if the determination section determines that the radiographic image has been imaged on the basis of a false detection of radiation.

In a twenty-first aspect of the present invention, in the above twentieth aspect, if it is determined by the determination section that the radiographic image for which the identification information has been generated has been imaged on the basis of a false detection of radiation and then a new radiographic image is imaged by the imaging section, then, without the identification information being generated at the first generation section, the first control section may control to associate image information of the new radiographic image imaged by the imaging section with the identification information identifying the image information of the radiographic image that the determination section has determined was imaged on the basis of a false detection of radiation, and to memorize the image information of the new radiographic image and the identification information at the first memory section.

In a twenty-second aspect of the present invention, in the above first aspect, the radiographic imaging device may include: the first memory section; an imaging section that includes the function for imaging the radiographic image; a first control section that controls to associate the image information with the identification information, and to memorize the same at the first memory section; a first transmission section that transmits the identification information to the handheld terminal device; and a first reception section that receives the association information and the identification information from the handheld terminal device, and the handheld terminal device may include: the second memory section; an acquisition section that acquires the imaging target information; a first generation section that generates the identification information; a second control section that controls to associate the imaging target information acquired by the acquisition section with the identification information, and to memorize the same at the second memory section; a second generation section that generates the association information in a case in which the imaging target information and the identification information have been associated and memorized by the second control section; and a second transmission section that transmits the association information generated by the second generation section to the radiographic imaging device.

A twenty-third aspect aspect of the invention is a radiographic imaging device including: an imaging section that images a radiographic image of an imaging target; a first generation section that generates identification information that identifies image information of the radiographic image; a first memory section at which the image information and the identification information generated by the first generation section are associated and memorized; a first control section that controls to associate the image information with the identification information generated by the first generation section, and to memorize the same at the first memory section; a first transmission section that transmits the identification information; and a first reception section that receives association information from a handheld terminal device, the association information indicating that imaging target information relating to the imaging target and the identification information have been associated and memorized.

A twenty-fourth aspect aspect of the invention is a handheld terminal device including: a second reception section that receives, from a radiographic imaging device, identification information that identifies image information of a radiographic image of an imaging target imaged by the radiographic imaging device; an acquisition section that acquires imaging target information relating to the imaging target; a second memory section at which the imaging target information acquired by the acquisition section and the identification information received by the second reception section are associated and memorized, a second control section that controls to associate the imaging target information acquired by the acquisition section with the identification information received by the second reception section, and to memorize the same at the second memory section; and a second transmission section that transmits association information to the radiographic imaging device in a case in which the imaging target information and the identification information have been associated and memorized by the second control section.

A twenty-fifth aspect aspect of the invention is a radiographic imaging method according to a radiographic imaging system that includes, a radiographic imaging device that images a radiographic image of an imaging target, a handheld terminal device, a first memory section at which image information of the radiographic image and identification information that identifies the image information are associated and memorized, and a second memory section, different from the first memory section, at which imaging target information relating to the imaging target and the identification information are associated and memorized, the radiographic imaging method including: generating, by the radiographic imaging device or the handheld terminal device, the identification information that identifies the image information of the radiographic image; associating, by the radiographic imaging device, the identification information with the image information, and memorizing the same at the first memory section; generating, by the handheld terminal device, association information and transmitting the association information to outside the handheld terminal device, in a case in which the imaging target information relating to the imaging target and the identification information have been associated and memorized at the second memory section that is different from the first memory section; and receiving, by the radiographic imaging device, the association information transmitted from the handheld terminal device.

According to the present invention, convenience for a user may be improved in a case of using the handheld terminal device to image a radiographic image.

BRIEF DESCRIPTION OF THE DRAWINGS

Exemplary embodiments of the present invention will be described in detail based on the following figures, wherein:

FIG. 4 is a descriptive diagram illustrating a state in which imaging device IDs, patient IDs and image IDs are associated and memorized in a memory section of the handheld terminal device;

FIG. 6 is a descriptive diagram illustrating a state in which image IDs and image data are associated and memorized in a memory section of the radiographic imaging device;

FIG. 12A, FIG. 12B and FIG. 12C are descriptive diagrams for describing specific examples in which states of radiographic imaging devices are displayed at a display of the handheld terminal device;

FIG. 13 is a flowchart illustrating the flow of processing of radiographic imaging relating to a radiographic imaging device in accordance with the third exemplary embodiment;

FIG. 27 is a flowchart illustrating the flow of processing of radiographic imaging in a case in which an image ID is generated by a handheld terminal device.

DETAILED DESCRIPTION OF THE INVENTION

Herebelow, present exemplary embodiments are described with reference to the attached drawings.

[First Exemplary Embodiment]

In the present exemplary embodiment, a radiographic imaging system is described for a case in which, before a radiographic imaging device images a radiographic image, an image ID (identification) is associated with a patient ID. The image ID is an example of identification information and the patient ID is an example of imaging target information. In the present exemplary embodiment, a case is described in which a radiographic imaging device 14 generates the image IDs.

Figure 1:
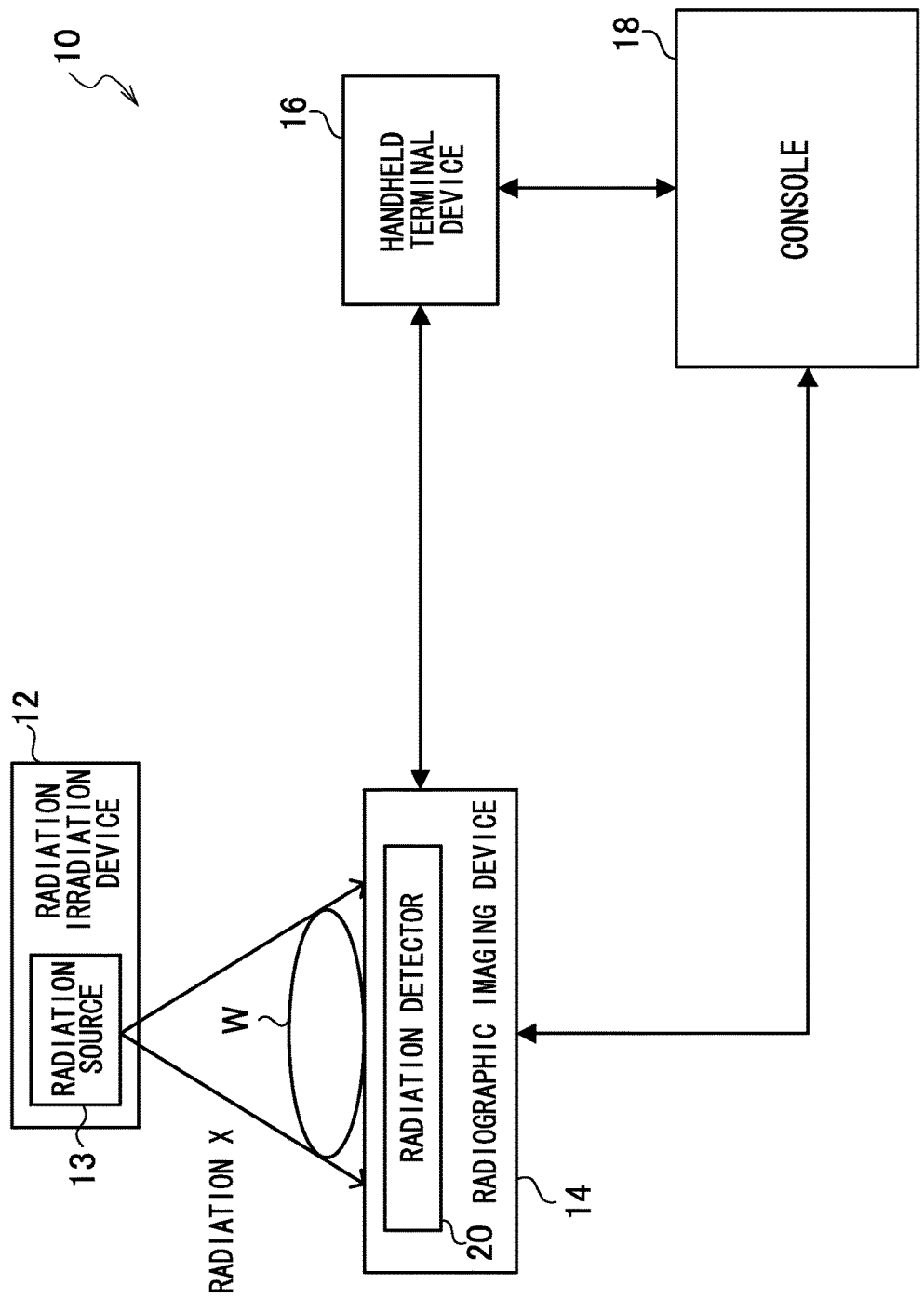
FIG. 1 is a schematic structural diagram showing schematic configuration of a radiographic imaging system in accordance with a first exemplary embodiment.

First, schematic configuration of a radiographic imaging system according to the present exemplary embodiment is described. FIG. 1 is a schematic structural diagram of the radiographic imaging system according to the present exemplary embodiment.

A radiographic imaging system 10 is provided with a radiation irradiation device 12, the radiographic imaging device 14, a handheld terminal device 16 and a console 18.

The radiation irradiation device 12 is equipped with a radiation source 13. The radiation irradiation device 12 includes a function for irradiating radiation X (for example, X-rays or the like) from the radiation source 13 at an imaging subject W, which is an example of an imaging target. As a specific example of the radiation irradiation device 12, a doctor's trolley or the like can be mentioned. An irradiation method for irradiating the radiation X from the radiation irradiation device 12 is not particularly limited. For example, in a case in which the radiation irradiation device 12 is equipped with an irradiation button or the like, the irradiation method may be a method in which a user such as a radiographer or the like commands irradiation with the irradiation button. As a further example, the irradiation method may be a method in which a user such as a radiographer or the like commands irradiation from the handheld terminal device 16. Herein, imaging subjects W are not limited to people but may be alternative organisms, including animals, and may be non-organic objects.

The radiographic imaging device 14 is equipped with a radiation detector 20 (described in detail below) that detects radiation X that has been irradiated from the radiation irradiation device 12 and passed through the imaging subject W. The radiographic imaging device 14 uses the radiation detector 20, which is an example of an imaging section, to image a radiographic image of the imaging subject W. Further, the radiographic imaging device 14 generates an image ID and transmitting the image ID to the handheld terminal device 16. The image ID is an example of identification information that identifies image data, which is image information of a radiographic image. Further, the radiographic imaging device 14 associates image data of an imaged radiographic image with a corresponding image ID and transmits the image data and image ID to the console 18. As a specific example of the radiographic imaging device 14, an electronic cassette may be applied.

The handheld terminal device 16 receives an image ID from the radiographic imaging device 14. The handheld terminal device 16 acquires a patient ID, which is an example of imaging target information relating to the imaging subject W, associates the patient ID with the image ID corresponding to the image data of a radiographic image in which the imaging subject W is imaged, and memorizes the patient ID and image ID. The handheld terminal device 16 permits the radiographic imaging device 14 to image a radiographic image in a case in which a patient ID and an image ID have been associated and memorized. The handheld terminal device 16 transmits an associated patient ID and image ID to the console 18. The handheld terminal device 16 according to the present exemplary embodiment may include some of the functions of the console 18 (for example, functions for controlling imaging of radiographic images). In the present exemplary embodiment, in a case in which the radiographic imaging device 14 has imaged a radiographic image, the handheld terminal device 16 does not receive image data of the imaged radiographic image in real time. The handheld terminal device 16 may be driven by a built-in battery. The handheld terminal device 16 is what is known as a PDA. As specific examples thereof, tablet terminals, smartphones and the like may be applied.

The console 18 controls the radiographic imaging system 10 as a whole in accordance with commands (imaging menu selections) inputted from an external system such as, for example, a radiology information system (RIS) or the like. The console 18 includes functions for controlling imaging of radiographic images. Accordingly, the console 18 accepts orders including imaging menu selections from the external system. In the present exemplary embodiment, an order is information including various commands relating to imaging of a radiographic image, specifically including a patient ID and an imaging menu selection.

With the radiographic imaging system 10 according to the present exemplary embodiment, in a case in which a radiographic image is to be imaged in a predetermined location, such as a ward, a sickbay, an operating room or the like, the radiation irradiation device 12, the radiographic imaging device 14 and the handheld terminal device 16 are disposed at the imaging location and the radiographic image is imaged. In contrast, the console 18 is disposed at another location (for example, a radiographic imaging room, a radiological examination room or the like) and conducts the imaging in this state.

Figure 2:
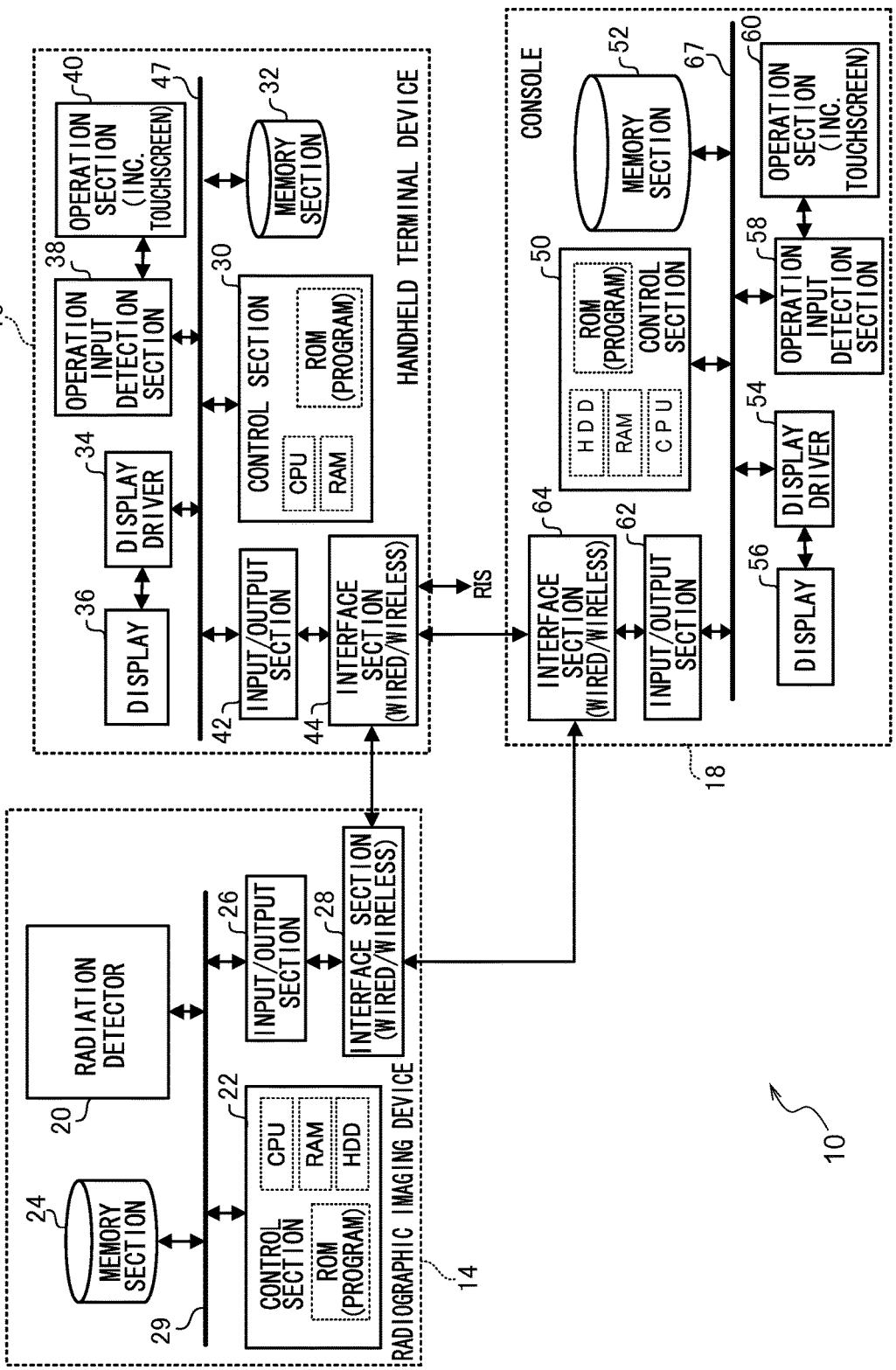
FIG. 2 is a functional block diagram showing schematic configurations of a radiographic imaging device, a handheld terminal device and a console of the radiographic imaging system in accordance with the first exemplary embodiment.

Now, the respective functions of the radiographic imaging device 14, the handheld terminal device 16 and the console 18 are described in detail. FIG. 2 is a functional block diagram showing schematic configurations of examples of the radiographic imaging device 14, the handheld terminal device 16 and the console 18.

The radiographic imaging device 14 according to the present exemplary embodiment is equipped with the radiation detector 20, a control section 22, a memory section 24, an input/output section 26 and an interface section 28. The radiation detector 20, the control section 22, the memory section 24 and the input/output section 26 are connected to be able to transfer information and the like to one another via a bus 29, which is a system bus, a control bus or the like.

The radiographic imaging device 14 according to the present exemplary embodiment is not particularly limited provided it includes a function for imaging a radiographic image in response to radiation X passing through an imaging subject W. For example, the start of an irradiation of the radiation X may be detected by an automatic device, and a radiographic image may be imaged without synchronization with the radiographic imaging device 14.

The radiation detector 20 includes a function for detecting the radiation X that has passed through the imaging subject W under the control of the control section 22. The radiation detector 20 according to the present exemplary embodiment is not particularly limited. For example, the radiation detector 20 may be an indirect conversion-type radiation detector that converts the radiation X to light and converts the converted light to electric charges, or the radiation detector 20 may be a direct conversion-type radiation detector that directly converts the radiation X to electric charges.

The control section 22 is an example of a first control section and a first generation section. The control section 22 controls operations of the radiographic imaging device 14. The control section 22 generates an image ID and transmits the image ID via the input/output section 26 and the interface section 28. The control section 22 associates image data of a radiographic image imaged by the radiation detector 20 with an image ID, and memorizes the image data and image ID in the memory section 24.

The control section 22 is provided with a central processing unit (CPU), read-only memory (ROM), random access memory (RAM) and a hard disk drive (HDD). The CPU controls the overall operations of the radiographic imaging device 14. Various processing programs and the like to be used at the CPU are pre-memorized in the ROM. The RAM temporarily stories various kinds of data. The HDD stores and retains various kinds of data. The HDD may be a solid state drive (SSD). The HDD may also be used as the memory section 24.

The memory section 24 is an example of a first memory section. The memory section 24 associates and memorizes image data of a radiographic image and an image ID under the control of the control section 22. An SSD (solid-state drive) or the like may be used as a specific example of the memory section 24. The memory section 24 may be integrated with the radiographic imaging device 14 in a case in which radiographic images are being imaged. For example, the radiographic imaging device 14 may be a universal serial bus (USB) memory, a Secure Digital (SD) memory card (registered trademark) or the like, and may be attachable to and detachable from the radiographic imaging device 14. Note that, the memory section 24 according to the present exemplary embodiment has enough capacity to memorize plural associated sets of image data and image IDs.

The input/output section 26 and interface section 28 are an example of a first transmission section and a first reception section. The input/output section 26 and interface section 28 include functions for exchanging various kinds of information with the handheld terminal device 16, the console 18 and the like, by wireless communications by electromagnetic waves, optical communications by light or the like. In the present exemplary embodiment, if no particular command has been given by a user or the like in a case in which a radiographic image is being imaged, the input/output section 26 and interface section 28 communicate with the handheld terminal device 16 by wireless. In the present exemplary embodiment, the term "wireless" includes near field communication (NFC), such as Felica (registered trademark) or the like.

The handheld terminal device 16 according to the present exemplary embodiment is provided with a control section 30, a memory section 32, a display driver 34, a display 36, an operation input detection section 38, an operation section 40, an input/output section 42 and an interface section 44. The control section 30, the memory section 32, the display driver 34, the operation input detection section 38 and the input/output section 42 are connected to transfer information and the like to one another via a bus 47, which is a system bus, a control bus or the like.

The control section 30 is an example of a second generation section, a second control section, an acquisition section, a third control section and a fourth control section. The control section 30 controls operations of the handheld terminal device 16 as a whole. The control section 30, in a case in which a patient ID is to be acquired from external equipment, such as the RIS, the console 18 or the like, acquires the patient ID via the input/output section 42 and the interface section 44. The control section 30 receives an image ID from the interface section 28 of the radiographic imaging device 14 via the input/output section 42 and the interface section 44, associates the received image ID with a patient ID, and memorizes the image ID and patient ID in the memory section 32.

The control section 30 is provided with a CPU, ROM and RAM. The CPU controls overall operations of the handheld terminal device 16. Various processing programs and the like to be used at the CPU are pre-memorized in the ROM. The RAM temporarily stores various kinds of data.

The display driver 34 controls the display of various kinds of information at the display 36. The display 36 according to the present exemplary embodiment is an example of a first display section and a second display section. The display 36 displays information relating to the radiographic imaging device 14, image IDs and the like. The operation input detection section 38 detects operation states and processes operations of the operation section 40. The operation section 40 is an example of an operation section and a designation section. The operation section 40 is used for a user to enter information relating to imaging of radiographic images, patient IDs and the like. The operation section 40 according to the present exemplary embodiment includes, for example, a touchscreen, a touch pen, plural buttons and a mouse, or the like. In a case in which the operation section 40 is a touchscreen, it may be the same component as the display 36.

The input/output section 42 and interface section 44 are an example of a second reception section, a second transmission section, a third reception section, a first acceptance section and a second acceptance section. The input/output section 42 and interface section 44 exchanges various kinds of information with the radiographic imaging device 14, the console 18 and the like, by wireless communications by electromagnetic waves, optical communications by light or the like. In the present exemplary embodiment, if no particular command has been given by a user or the like in a case in which a radiographic image is being imaged, the input/output section 42 and interface section 44 communicate with the radiographic imaging device 14 by wireless.

The memory section 32 is an example of a second memory section and a third memory section. The memory section 32 associates and memorizes a patient ID and an image ID under the control of the control section 30. A non-volatile memory or the like can be mentioned as a specific example of the memory section 32. The memory section 32 according to the present exemplary embodiment employs a memory with a relatively small capacity. Specifically, the memory section 32 employs a memory with a smaller capacity than the memory section 24 of the radiographic imaging device 14. A memory with a smaller capacity of the data to be memorized than the memory section 24 of the radiographic imaging device 14 may be employed because the handheld terminal device 16 according to the present exemplary embodiment does not need to memorize image data of radiographic images.

The console 18 according to the present exemplary embodiment is a server computer. The console 18 includes a control section 50, a memory section 52, a display driver 54, a display 56, an operation input detection section 58, an operation section 60, an input/output section 62 and an interface section 64. The control section 50, the memory section 52, the display driver 54, the operation input detection section 58 and the input/output section 62 are connected to be able to transfer information and the like to one another via a bus 67, which is a system bus, a control bus or the like.

The control section 50 is an example of the third control section. The control section 50 controls overall operations of the console 18, and is provided with a CPU, ROM, RAM and an HDD. The CPU controls the overall operations of the console 18. Various processing programs and the like to be used at the CPU are pre-memorized in the ROM. The RAM temporarily stores various kinds of data. The HDD stores and retains various kinds of data.

The display driver 54 controls the display of various kinds of information at the display 56. The display 56 according to the present exemplary embodiment displays radiographic images according to image data and the like. The operation input detection section 58 detects operation states and processes operations of the operation section 60. The operation panel 60 is used for a user to enter information relating to imaging of radiographic images, patient IDs and the like. The operation panel 60 according to the present exemplary embodiment includes, for example, a touchscreen, a touch pen, plural buttons and a mouse, or the like. In a case in which the operation panel 60 is a touchscreen, it may be the same component as the display 56.

The input/output section 62 and interface section 64 are an example of the third reception section. The input/output section 62 and interface section 64 include functions for exchanging various kinds of information with the radiographic imaging device 14, the handheld terminal device 16 and the like, by wireless communications by electromagnetic waves, optical communications by light or the like.

The memory section 52 is an example of the third memory section. The memory section 52 associates and memorizes a patient ID, an image ID and image data under the control of the control section 50. A non-volatile memory or the like may be applied as a specific example of the memory section 52. The memory section 52 according to the present exemplary embodiment employs a memory with a relatively large capacity, because the memory section 52 is to be capable of memorizing plural associated sets of image data, patient IDs and image IDs. Specifically, the capacity of the memory section 52 is at least larger than the memory section 32 of the handheld terminal device 16, and is more preferably larger than the memory section 24 of the radiographic imaging device 14.

Now, operation of the radiographic imaging system 10 in imaging of a radiographic image by the radiographic imaging system 10 according to the present exemplary embodiment is described. As mentioned above, in a case in which imaging is to be performed with the radiographic imaging system 10 in a ward or the like, the imaging is performed without the console 18 being disposed at the imaging location. Accordingly, operations of the radiographic imaging device 14 and the handheld terminal device 16 are described here.

In a case in which a radiographic image is to be imaged, firstly, the radiographic imaging device 14 and handheld terminal device 16 to be used for the imaging are put into an associated state. In the present exemplary embodiment, the state in which the radiographic imaging device 14 and handheld terminal device 16 to be used for the imaging are associated thus is referred to as the "effective" state.

Figure 3:
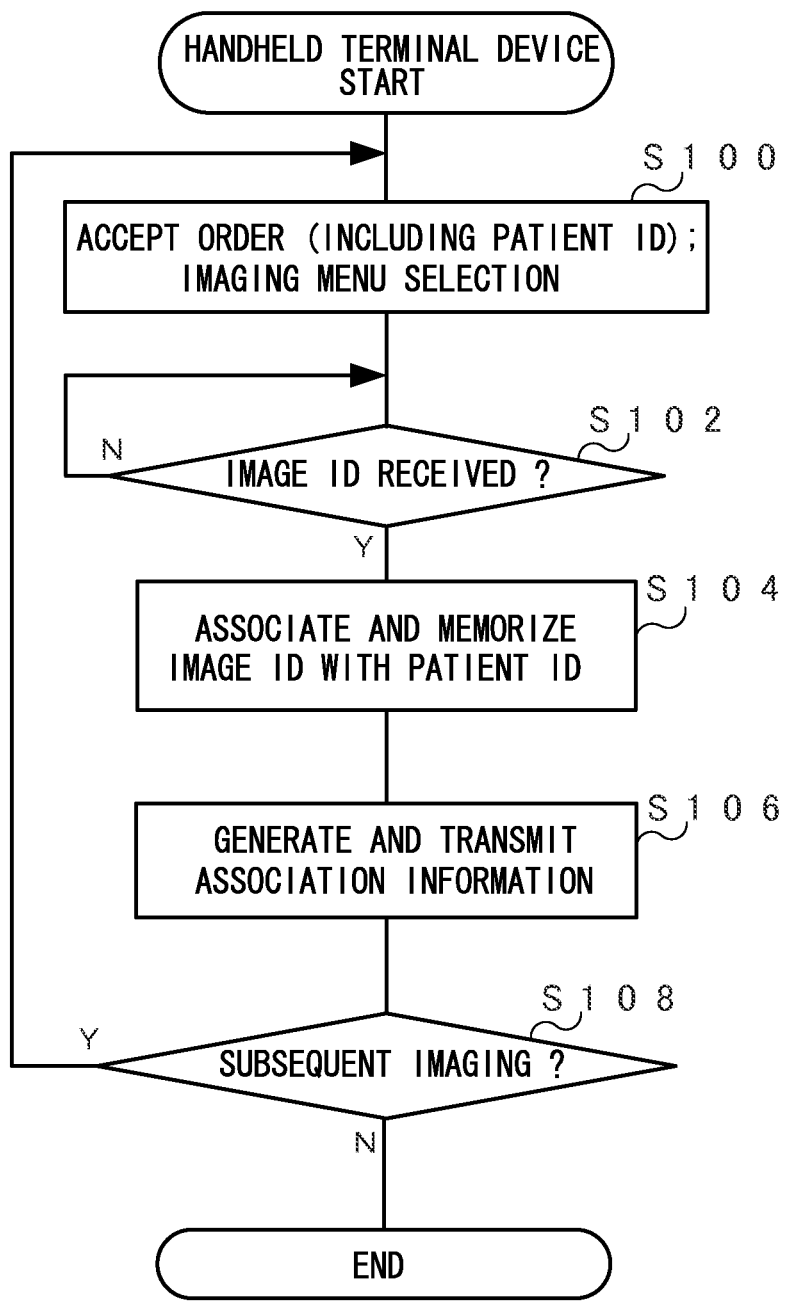
FIG. 3 is a flowchart illustrating the flow of processing of radiographic imaging relating to the handheld terminal device in accordance with the first exemplary embodiment.

In a case in which the handheld terminal device 16 is put into the effective state, the handheld terminal device 16 executes the processing shown in FIG. 3. FIG. 3 shows a flowchart illustrating the flow of an example of processing that is executed by the control section 30 of the handheld terminal device 16 according to the present exemplary embodiment. In the handheld terminal device 16 according to the present exemplary embodiment, the control section 30 functions as respective functional sections of the present invention, and executes the processing shown in FIG. 3 by executing a processing program memorized in the ROM thereof.

In step S100, the control section 30 accepts an order including a patient ID, and selects an imaging menu selection. The order may be accepted from the RIS via the input/output section 42 and interface section 44, or may be accepted from the console 18. An order that a user enters with the operation section 40 may also be accepted, via the operation input detection section 38.

Then, in step S102, the control section 30 makes a determination as to whether an image ID has been received. The control section 30 continues to wait until an image ID is received from the radiographic imaging device 14. In a case in which an image ID has been received via the input/output section 42 and interface section 44, the control section 30 proceeds to step S104. Information identifying the radiographic imaging device 14 may be received in addition to the image ID. The information identifying the radiographic imaging device 14 may be, for example, an imaging device ID or the like. Hereinafter, the information identifying the radiographic imaging device 14 is referred to as "the imaging device ID". Thus, in a case in which the handheld terminal device 16 receives respective image IDs from a plural number of the radiographic imaging device 14, the handheld terminal device 16 may distinguish the radiographic imaging devices 14 by their imaging device IDs, due to having received the imaging device IDs and memorized the same in the memory section 32.

In step S104, the control section 30 associates the image ID with the patient ID and memorizes the same in the memory section 32. In a case in which an imaging device ID is received as described above, the imaging device ID is also associated and memorized in the memory section 32. In a case in which an imaging device ID of a radiographic imaging device 14 that has been used for previous imaging is known, this imaging device ID may similarly be associated and memorized in the memory section 32. As a specific example, FIG. 4 shows a state in which imaging device IDs, patient IDs and image IDs are associated and memorized in the memory section 32.

Then, in step S106, the control section 30 generates association information, which is information representing the association of the image ID with the patient ID, and transmits the association information to the radiographic imaging device 14 via the input/output section 42 and interface section 44. The association information is not particularly limited to the above, and may be any information unless it represents an association of an image ID with a patient ID, but is preferable to be information with a small data volume.

By transmitting the association information to the radiographic imaging device 14, the handheld terminal device 16 according to the present exemplary embodiment gives the radiographic imaging device 14 permission to carry out imaging of a radiographic image.

Then, in step S108, the control section 30 makes a determination as to whether subsequent imaging is to be performed. For example, in a case in which there is a command relating to subsequent imaging or the like, the control section 30 determines that subsequent imaging is to be performed, returns to step S100, and repeats the present processing. On the other hand, if there is no subsequent imaging, the control section 30 ends the present processing.

Figure 5:
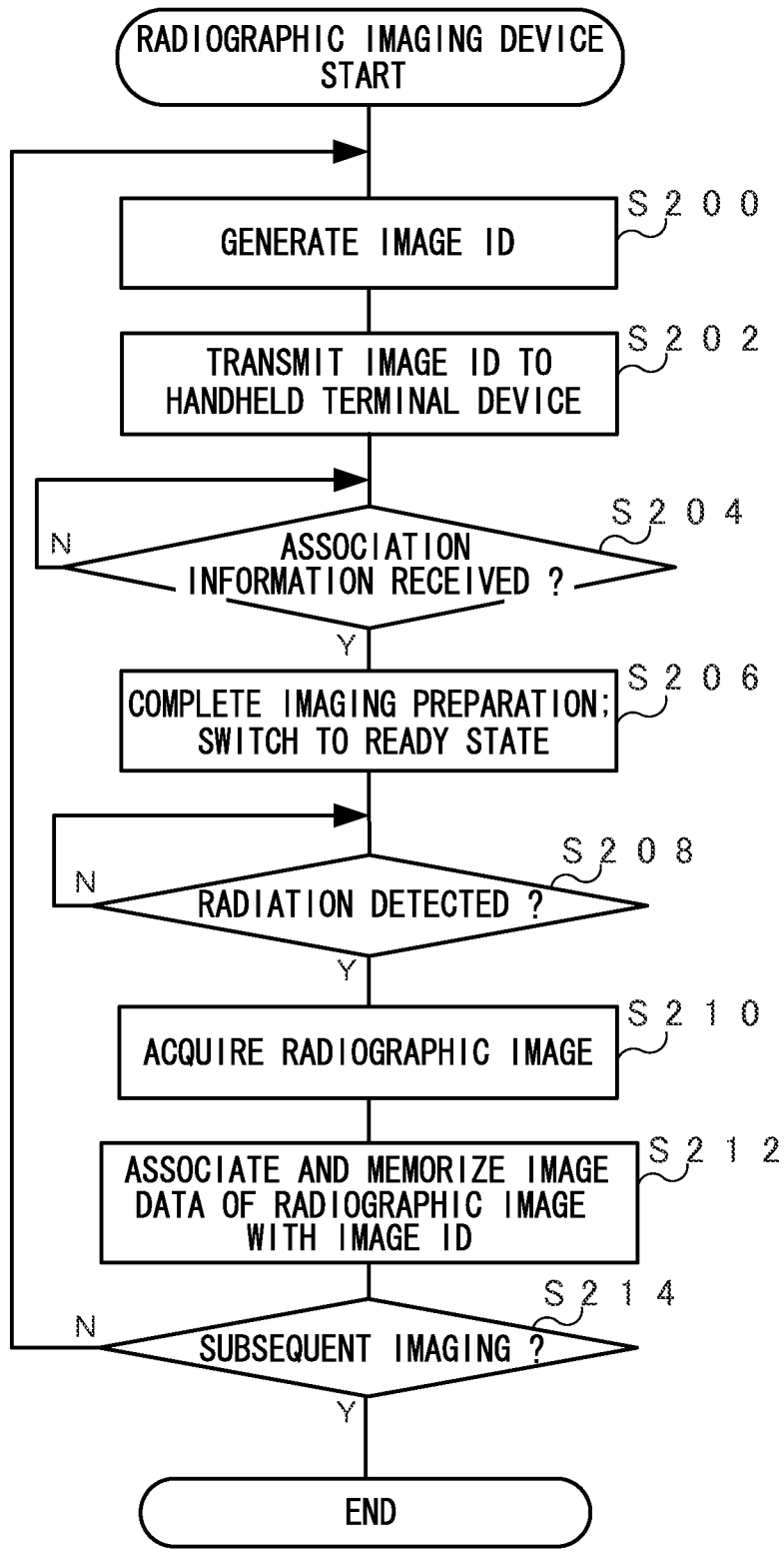
FIG. 5 is a flowchart illustrating the flow of processing of radiographic imaging relating to the radiographic imaging device in accordance with the first exemplary embodiment.

Meanwhile, in a case in which the radiographic imaging device 14 is put into the effective state, the processing shown in FIG. 5 is executed. FIG. 5 shows a flowchart illustrating the flow of an example of processing that is executed by the control section 22 of the radiographic imaging device 14 according to the present exemplary embodiment. In the radiographic imaging device 14 according to the present exemplary embodiment, the control section 22 functions as respective functional sections of the present invention, and executes the processing shown in FIG. 5 by executing a processing program memorized in the ROM thereof.

In step S200, the control section 22 generates an image ID. The image ID is not particularly limited to the above, and may be information with which a radiographic image may be distinguished. However, information with a small data volume is preferable.

Then, in step S202, the control section 22 transmits the image ID to the handheld terminal device 16 via the input/output section 26 and the interface section 28.

Then, in step S204, the control section 22 makes a determination as to whether association information has been received from the handheld terminal device 16 via the input/output section 26 and interface section 28. The control section 22 continues to wait until the association information transmitted in step S106 of the processing at the handheld terminal device 16 described above is received. In a case in which the association information is received, the control section 22 proceeds to step S206. If the association information has not been received after a predetermined duration has passed since the control section 22 transmitted the image ID to the handheld terminal device 16, the control section 22 may assume that some kind of error has occurred and perform predetermined error processing, which is processing to, for example, provide a warning to a user or the like.

In step S206, the control section 22 obtains imaging permission from the handheld terminal device 16 by receiving the association information. Hence, the control section 22 completes imaging preparation. Consequent to imaging preparation being completed, the control section 22 permits imaging of a radiographic image by the radiation detector 20, and puts the radiation detector 20 into a ready state. In the present exemplary embodiment, the term "ready state" refers to a state in which the radiation X can be detected immediately. In the present exemplary embodiment, a state in which a power supply is turned ON but the radiation detector 20 is not in the effective state or the ready state, is referred to as "the idle state".

Then, in step S208, the control section 22 makes a determination as to whether the radiation detector 20 has detected the radiation X. The control section 22 stays in the ready state until the radiation X is detected, and proceeds to step S210 if the radiation X is detected.

In step S210, the control section 22 acquires a radiographic image (image data) from the radiation detector 20.

Then, in step S212, the control section 22 associates the image data of the radiographic image with the image ID generated in step S200 and memorizes the same in the memory section 24. As a specific example, FIG. 6 illustrates a state in which image IDs and sets of image data are associated and memorized in the memory section 24.

Then, in step S214, the control section 22 makes a determination as to whether subsequent imaging is to be performed. For example, in a case in which there is a command relating to subsequent imaging or the like, the control section 22 determines that subsequent imaging is to be performed, returns to step S200, and repeats the present processing. On the other hand, if there is no subsequent imaging, the control section 22 ends the present processing. If the present processing is not to end after the acquisition of a radiographic image, the radiographic imaging device 14 according to the present exemplary embodiment switches back from the ready state to the effective state, but if the present processing is to end, the radiographic imaging device 14 switches back from the ready state to the idle state.

Thus, before imaging of a radiographic image, the handheld terminal device 16 according to the present exemplary embodiment receives an image ID from the radiographic imaging device 14, associates a patient ID with the image ID, and memorizes the same in the memory section 32. Hence, in a case in which the radiographic imaging device 14 receives the association information transmitted from the handheld terminal device 16, the radiographic imaging device 14 images the radiographic image, and associates and memorizes the image ID with image data of the radiographic image.

Figure 7:
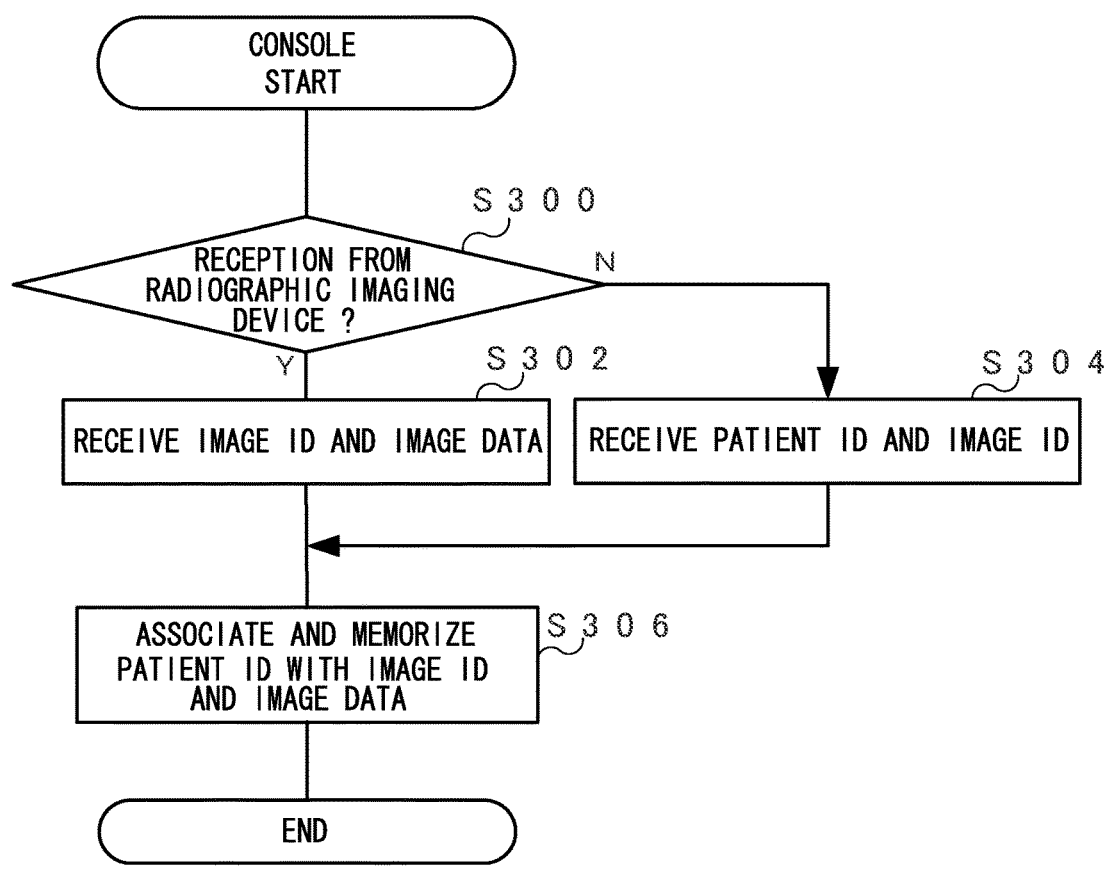
FIG. 7 is a flowchart illustrating the flow of processing of radiographic imaging relating to the console in accordance with the first exemplary embodiment.

In a case in which the console 18 receives an image ID and image data from the radiographic imaging device 14 and receives a patient ID and image ID from the handheld terminal device 16, the console 18 associates and memorizes the patient ID, the image ID and the image data. An example of processing that is executed by the console 18 is described. FIG. 7 shows a flowchart illustrating the flow of the example of the processing that is executed by the control section 50 of the console 18 according to the present exemplary embodiment. In the console 18 according to the present exemplary embodiment, the control section 50 functions as respective functional sections of the present invention, and executes the processing shown in FIG. 7 by executing a processing program memorized in the ROM thereof.

The console 18 executes the processing shown in FIG. 7 in a case in which information is received from the radiographic imaging device 14 or the handheld terminal device 16 via the input/output section 62 and the interface section 64.

In step S300, the control section 50 makes a determination as to whether the information has been received from the radiographic imaging device 14. In a case in which the information has been received from the radiographic imaging device 14, the control section 50 proceeds to step S302. Information to be received from the radiographic imaging device 14 is an associated image ID and image data. Accordingly, in step S302 the control section 50 receives the image ID and image data, and then proceeds to step S306.

On the other hand, in a case in which information has been received from the handheld terminal device 16, the control section 50 proceeds to step S304. In the case of information received from the handheld terminal device 16, the information is an associated patient ID and image ID. Accordingly, in step S304 the control section 50 receives the patient ID and image ID, and then proceeds to step S306.

In step S306, the control section 50 associates the patient ID, image ID and image data and memorizes the same in the memory section 52. Then the control section 50 ends the present processing.

Thus, in the radiographic imaging system 10 according to the present exemplary embodiment, patient IDs and image data may be suitably associated at the console 18 on the basis of image IDs.

[Second Exemplary Embodiment]

In the radiographic imaging system 10 according to the first exemplary embodiment, the handheld terminal device 16 associates an image ID with a patient ID before a radiographic image is imaged. However, in the radiographic imaging system 10 according to the present exemplary embodiment, the radiographic imaging device 14 associates an image ID with a patient ID after imaging of a radiographic image.

The radiographic imaging system 10 according to the present exemplary embodiment is provided with similar configurations and operations to the radiographic imaging system 10 according to the first exemplary embodiment. Accordingly, detailed descriptions of portions that are the same are omitted.

The configurations of the radiation irradiation device 12, the radiographic imaging device 14, the handheld terminal device 16 and the console 18 are the same as in the first exemplary embodiment. Therefore, description regarding these configurations will be omitted in the present exemplary embodiment.

Operations of the radiographic imaging system 10 in imaging of a radiographic image by the radiographic imaging system 10 according to the present exemplary embodiment are described.

In the present exemplary embodiment too, in a case in which a radiographic image is to be imaged, firstly, the radiographic imaging device 14 and handheld terminal device 16 to be used for the imaging are put into the effective state.

Figure 8:
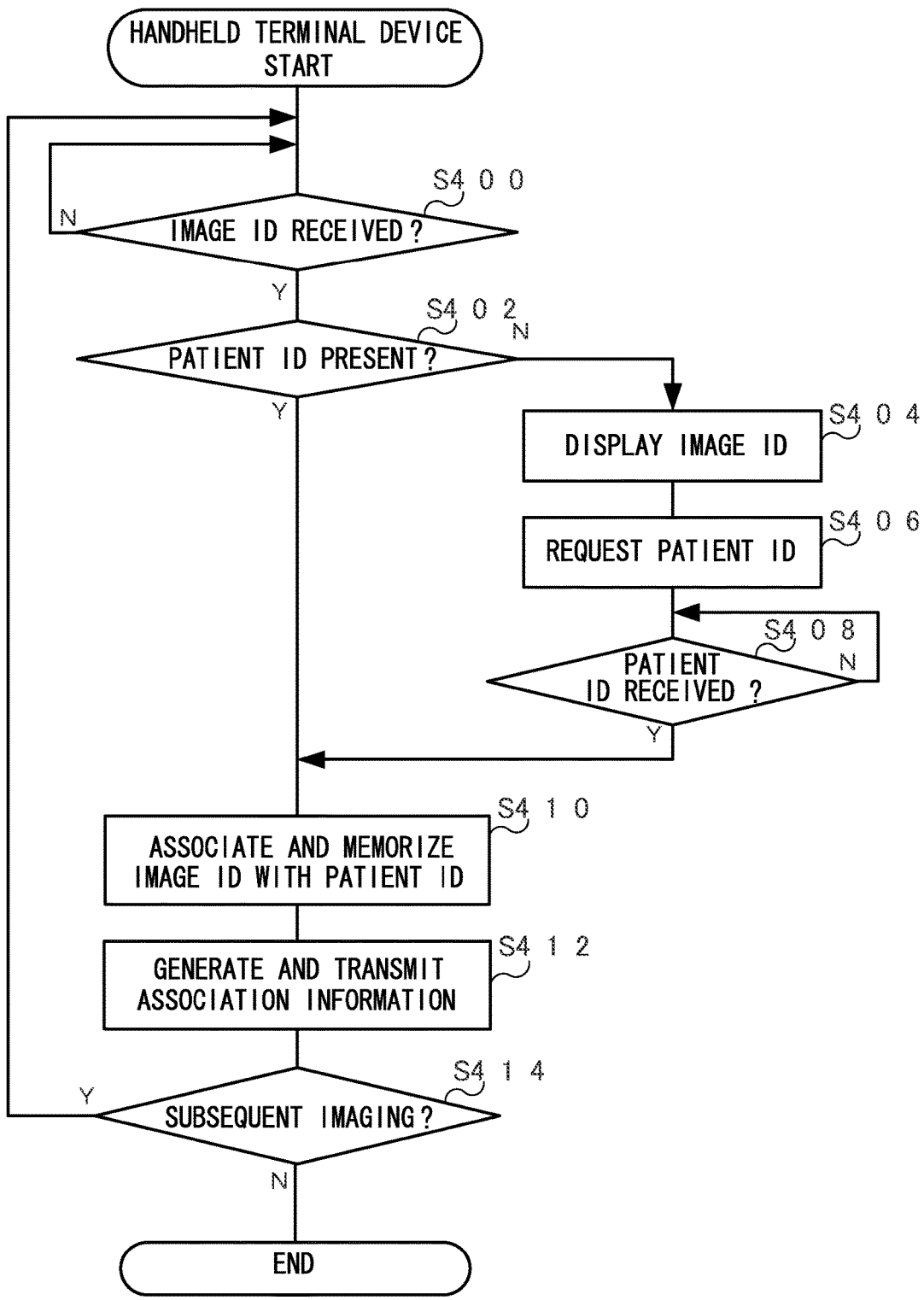
FIG. 8 is a flowchart illustrating the flow of processing of radiographic imaging relating to a handheld terminal device in accordance with a second exemplary embodiment.

In a case in which the handheld terminal device 16 is put into the effective state, the handheld terminal device 16 executes the processing shown in FIG. 8. FIG. 8 shows a flowchart illustrating the flow of an example of processing that is executed by the control section 30 of the handheld terminal device 16 according to the present exemplary embodiment.

In step S400, the control section 30 makes a determination as to whether an image ID has been received. The control section 30 continues to wait until an image ID is received from the radiographic imaging device 14. In a case in which an image ID has been received via the input/output section 42 and interface section 44, the control section 30 proceeds to step S402. In the present exemplary embodiment, this is a state in which the imaging of the radiographic image has already been implemented and image data has been acquired at the radiographic imaging device 14.

In step S402, the control section 30 makes a determination as to whether a patient ID is present. If, for example, no patient ID has been received from external equipment or the console 18, there is no patient ID. Accordingly, the control section 30 proceeds to step S404.

In step S404, the control section 30 displays the received image ID at the display 36 with the display driver 34.

Then, in step S406, with the display driver 34, the control section 30 displays an indication at the display 36 that a patient ID corresponding to the displayed image ID is required. In response to the display of the indication that a patient ID is required, the user uses the operation section 40 to enter a patient ID.

A case has been described in which there is no patient ID in steps S402 to S406. However, the control section 30 may act similarly in a case in which there are plural patient IDs and a patient ID for the imaging subject W that is being imaged has not been designated from among the plural patient IDs. Specifically, in step S402, the control section 30 makes a determination as to whether there is a designated patient ID among plural patient IDs that are present. If no patient ID is designated, then in step S406 the control section 30 displays an indication at the display 36 requesting that a patient ID be designated, prompting the user to designate the patient ID with the operation section 40. If no patient ID is designated, it is preferable if the radiographic imaging device 14 does not go into the ready state and that a display at the display 36 representing the state of the radiographic imaging device 14 (see indicators 72A to 72C, which are described in detail below) is not set to represent the ready state but to represent the idle state or the effective state. Thus, the radiographic imaging device 14 does not go into the ready state until a patient ID is designated. As a result, erroneous associations of patient IDs with image IDs may be suppressed.

Then, in step S408, the control section 30 makes a determination as to whether a patient ID has been received. If no patient ID has been received, the control section 30 continues to wait, but if a patient ID has been received, the control section 30 proceeds to step S410.

On the other hand, if there is a patient ID at step S402, the control section 30 proceeds from step S402 to step S410.

In step S410, the control section 30 associates the image ID with the patient ID and memorizes the same in the memory section 32.

Then, in step S412, the control section 30 generates association information and transmits the association information to the radiographic imaging device 14 via the input/output section 42 and interface section 44. Thus, by transmitting the association information to the radiographic imaging device 14, the handheld terminal device 16 according to the present exemplary embodiment gives the radiographic imaging device 14 permission to image a subsequent radiographic image.

Then, in step S414, the control section 30 makes a determination as to whether subsequent imaging is to be performed. For example, in a case in which there is a command relating to subsequent imaging or the like, the control section 30 determines that subsequent imaging is to be performed, returns to step S400, and repeats the present processing. On the other hand, if there is no subsequent imaging, the control section 30 ends the present processing.

Figure 9:
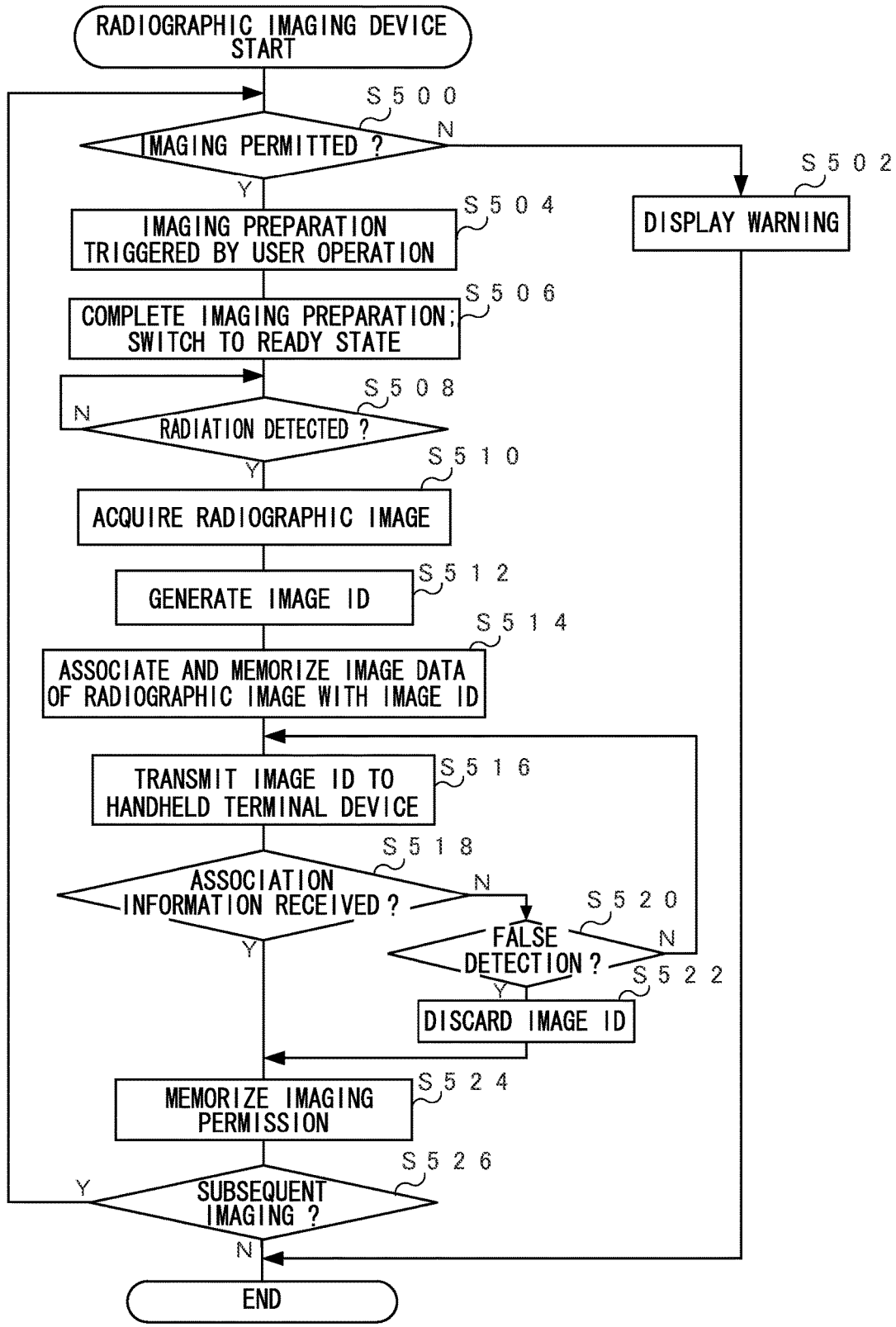
FIG. 9 is a flowchart illustrating the flow of processing of radiographic imaging relating to a radiographic imaging device in accordance with the second exemplary embodiment.

Meanwhile, in a case in which the radiographic imaging device 14 is put into the effective state, the processing shown in FIG. 9 is executed. FIG. 9 shows a flowchart illustrating the flow of an example of processing that is executed by the control section 22 of the radiographic imaging device 14 according to the present exemplary embodiment.

In step S500, the control section 22 makes a determination as to whether imaging permission has been provided from the handheld terminal device 16. It is preferable to display information as to whether imaging at the radiographic imaging device 14 is permitted or not at the display 36 of the handheld terminal device 16. If imaging corresponding to a previous image has not been implemented, such as in a case in which a first radiographic image is to be imaged by the radiographic imaging device 14 or the like, it may be assumed that imaging permission is given and the present processing may be omitted.

If there is no imaging permission, the control section 22 proceeds to step S502, prohibits imaging by the radiation detector 20 and/or displays a warning, and then ends the present processing. The display of a warning may be a display at a display unit with which the radiographic imaging device 14 can display a warning indication (which is not limited to a display but may be a light emitting diode (LED) or the like). The display of a warning may also be transmitted to the handheld terminal device 16 via the input/output section 26 and interface section 28 so as to be displayed at the handheld terminal device 16.

Then, in step S504, preparation for imaging begins by using a user operation as a trigger. The user operation may be carried out directly at the radiographic imaging device 14, or may be carried out via the handheld terminal device 16.

Then, in step S506, the control section 22 completes imaging preparation and puts the radiation detector 20 into the ready state.

Then, in step S508, the control section 22 makes a determination as to whether the radiation detector 20 has detected the radiation X. The control section 22 stays in the ready state until the radiation X is detected, and proceeds to step S510 if the radiation X is detected.

In step S510, the control section 22 acquires a radiographic image (image data) from the radiation detector 20.

Then, in step S512, the control section 22 generates an image ID. In step S514, the control section 22 associates the image data of the radiographic image with the image ID generated in step S512, and memorizes the same in the memory section 24.

In step S516, the control section 22 transmits the image ID to the handheld terminal device 16 via the input/output section 26 and interface section 28.

Then, in step S518, the control section 22 makes a determination as to whether the association information has been received. If the association information transmitted in step S412 of the above-described processing at the handheld terminal device 16 has not been received, the control section 22 proceeds to step S520. In step S520, the control section 22 makes a determination as to whether the radiation detector 20 has falsely detected the radiation X. There may be cases in which the radiation X is falsely detected by the radiographic imaging device 14 (the radiation detector 20) according to the present exemplary embodiment. For example, there may be cases in which radiation X caused by noise or the like is irradiated and falsely detected even though the radiation X is not actually being irradiated from the radiation irradiation device 12. In such a case, the control section 22 determines that the radiation has been falsely detected and proceeds to step S522. In step S522, because a radiographic image has not actually been imaged, the control section 22 discards the generated image ID, and then proceeds to step S524. In this case, the image data that has been associated and memorized in the above-described step S514 is also discarded. A method of determining whether there has been a false detection or not is not particularly limited; it is acceptable to use a previous method.

On the other hand, if there has not been a false detection, the control section 22 returns from step S520 to step S516 and again transmits the image ID to the handheld terminal device 16. If the image ID cannot be transmitted to the handheld terminal device 16 even in a case in which the image ID has been transmitted a predetermined number of times (re-transmitted), information indicating that the transmission was not possible is associated with the image ID and the image data and memorized in the memory section 24.

Alternatively, if the association information has been received, the control section 22 proceeds from step S518 to step S524.

In step S524, the control section 22 memorizes the fact that imaging permission has been given in, for example, the memory section 24.

Then, in step S526, the control section 22 makes a determination as to whether subsequent imaging is to be performed. For example, in a case in which there is a command relating to subsequent imaging or the like, the control section 22 determines that subsequent imaging is to be performed, returns to step S500, and repeats the present processing. On the other hand, if there is no subsequent imaging, the control section 22 ends the present processing. If the present processing is not to end after the acquisition of a radiographic image, the radiographic imaging device 14 according to the present exemplary embodiment switches back from the ready state to the effective state, but if the present processing is to end, the radiographic imaging device 14 returns to the idle state.

The processing at the console 18 according to the present exemplary embodiment that associates the patient ID, the image ID and the image data and memorizes the same in the memory section 52 is the same as in the first exemplary embodiment, so description thereof will be omitted.

Thus, the radiographic imaging device 14 according to the present exemplary embodiment generates an image ID and associates and memorizes the image ID with image data of a radiographic image after the imaging of the radiographic image. The radiographic imaging device 14 also transmits the generated image ID to the handheld terminal device 16. At the handheld terminal device 16, after the imaging of the radiographic image, the patient ID and the image ID are associated and memorized in the memory section 32.

Thus, in the radiographic imaging system 10 according to the present exemplary embodiment, patient IDs and image data may be suitably associated at the console 18 on the basis of image IDs.

[Third Exemplary Embodiment]

Cases have been described in which the radiographic imaging system 10 according to each exemplary embodiment described above is provided with one each of the radiographic imaging device 14 and the handheld terminal device 16. In contrast, a case in which a plural number of the radiographic imaging devices 14 are provided in the radiographic imaging system 10 according to the present exemplary embodiment is described.

The radiographic imaging system 10 according to the present exemplary embodiment is provided with similar configurations and operations to the radiographic imaging system 10 according to each exemplary embodiment described above. Accordingly, detailed descriptions of portions that are the same will be omitted.

Figure 10:
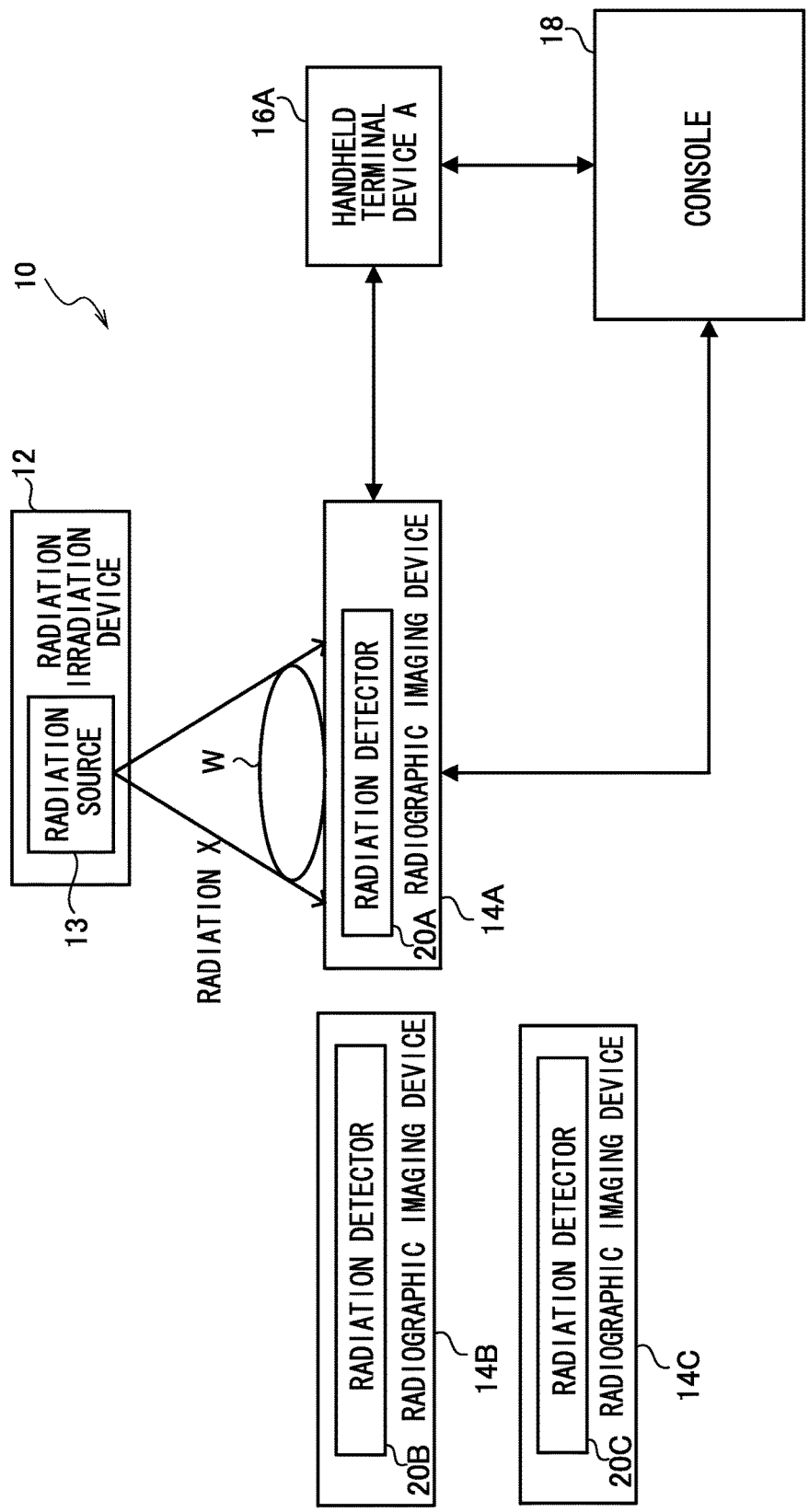
FIG. 10 is a schematic structural diagram showing schematic configuration of a radiographic imaging system in accordance with a third exemplary embodiment.

FIG. 10 is a schematic structural diagram of an example of a radiographic imaging system according to the present exemplary embodiment.

The radiographic imaging system 10 according to the present exemplary embodiment is provided with a plural number of the radiographic imaging device 14 (14A, 14B and 14C), as illustrated in FIG. 10. Hereinafter, in cases in which the radiographic imaging devices 14A, 14B and 14C are referred to in general without being individually distinguished, they are referred to as "the radiographic imaging device(s) 14". In the present exemplary embodiment, a case in which three of the radiographic imaging devices 14 are provided is described as a specific example, but the number of the radiographic imaging devices 14 to be provided is not particularly limited.

The radiographic imaging device 14A is provided with a radiation detector 20A, the radiographic imaging device 14B is provided with a radiation detector 20B, and the radiographic imaging device 14C is provided with a radiation detector 20C. Hereinafter, in cases in which the radiation detectors 20A, 20B and 20C are referred to in general without being individually distinguished, they are referred to as "the radiation detector(s) 20".

In the present exemplary embodiment, the radiographic imaging devices 14A, 14B and 14C that are used are of the same type (with the same configurations), but types of the radiographic imaging devices 14 are not particularly limited; they may be of the same type and they may be of different types.

Configurations relating to the respective functions of the radiation irradiation device 12, the radiographic imaging devices 14, the handheld terminal device 16 and the console 18 are the same as in the exemplary embodiments described above, so are not described for the present exemplary embodiment.

Operations of the handheld terminal device 16 according to the present exemplary embodiment are described.

Figure 11:
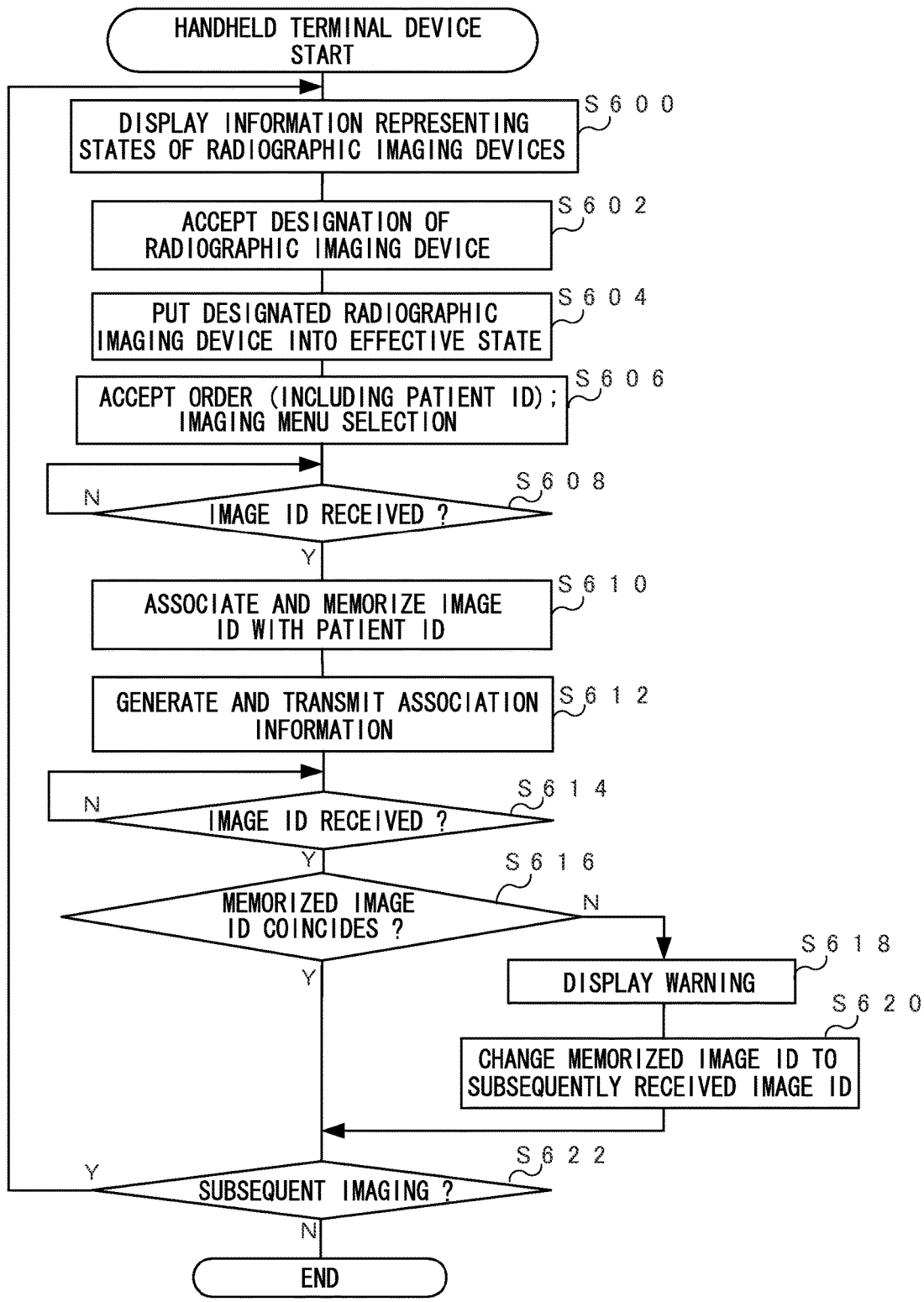
FIG. 11 is a flowchart illustrating the flow of processing of radiographic imaging relating to a handheld terminal device in accordance with the third exemplary embodiment.

The handheld terminal device 16 executes the processing shown in FIG. 11. FIG. 11 shows a flowchart illustrating the flow of an example of processing that is executed by the control section 30 of the handheld terminal device 16 according to the present exemplary embodiment. In the handheld terminal device 16 according to the present exemplary embodiment, the control section 30 functions as respective functional sections of the present invention, and executes the processing shown in FIG. 11 by executing a processing program memorized in the ROM thereof.

In step S600, the control section 30 displays information representing states of the radiographic imaging devices 14 at the display 36, with the display driver 34. At this time, it is sufficient to display information representing the state of each radiographic imaging device 14 for which a power supply has been turned on, each radiographic imaging device 14 that has been registered beforehand at the handheld terminal device 16, or the like. In the present exemplary embodiment, specifically, information representing the state of each radiographic imaging device 14 that has access to an access point of the handheld terminal device 16 is displayed.

A specific example of states of the radiographic imaging devices 14 being displayed at the display 36 is shown in FIG. 12A to FIG. 12C. FIG. 12A to FIG. 12C show states in which the indicator 72A, representing the state of the radiographic imaging device 14A, the indicator 72B, representing the state of the radiographic imaging device 14B, and the indicator 72C, representing the state of the radiographic imaging device 14C, are displayed at the display 36. In FIG. 12A, it is indicated that all of the radiographic imaging devices 14 are in the idle state. In FIG. 12B, it is indicated by the indicator 72A that the radiographic imaging device 14A is in the effective state. In FIG. 12C, it is indicated by the indicator 72A that the radiographic imaging device 14A is in the ready state. The display 36 according to the present exemplary embodiment may be a touchscreen that is combined with the operation section 40. Thus, the states of the radiographic imaging devices 14 may be designated (or changed) by the indicators 72A to 72C being touched.

Then, in step S602, the control section 30 accepts a designation of the radiographic imaging devices 14 that a user designates with the indicators 72A to 72C of the display 36 (the operation section 40). Herein, as a specific example, it is assumed that the user designates plural devices of the radiographic imaging devices 14.

In step S604, the control section 30 puts the designated radiographic imaging devices 14 into the effective state. In step S606, the control section 30 accepts an order including a patient ID, and selects an imaging menu selection. Although not shown in the drawings, in the present exemplary embodiment the control section 30 commands each radiographic imaging device 14 such that the radiographic imaging device 14 goes into the ready state.

Then, in step S608, the control section 30 makes a determination as to whether an image ID has been received.

The control section 30 continues to wait until an image ID is received from one of the radiographic imaging devices 14. If an image ID has been received via the input/output section 42 and interface section 44, the control section 30 proceeds to step S610. An imaging device ID may be received in addition to the image ID. Particularly in the radiographic imaging system 10 according to the present exemplary embodiment, because a plural number of the radiographic imaging devices 14 are present, it is preferable to receive the imaging device ID from the radiographic imaging device 14 with the image ID.

In step S610, the control section 30 associates the image ID with the patient ID and memorizes the same in the memory section 32. In a case in which an imaging device ID is received as described above, the imaging device ID is also associated and memorized in the memory section 32. In a case in which an imaging device ID of a radiographic imaging device 14 that has been used for previous imaging is known, this imaging device ID may similarly be associated and memorized in the memory section 32.

Then, in step S612, the control section 30 generates association information and transmits the association information to the radiographic imaging device 14 via the input/output section 42 and interface section 44.

Then, in step S614, the control section 30 makes a determination as to whether an image ID has been received. The control section 30 continues to wait until an image ID is received from one of the radiographic imaging devices 14. In the present exemplary embodiment, as is described below, the radiographic imaging device 14 transmits the image ID again after imaging the radiographic image. Accordingly, in a case in which an image ID has been received via the input/output section 42 and interface section 44, the control section 30 proceeds to step S616.

In step S616, the control section 30 makes a determination as to whether the image ID received in step S614 coincides with an image ID memorized in the memory section 32. In the present exemplary embodiment, as mentioned above, the user designates plural devices of the radiographic imaging devices 14 in addition to the radiographic imaging device 14 that is intended to image the radiographic image. The plural radiographic imaging devices 14 are put into the effective state by this designation, and then put into the ready state. Consequently, it may be that a radiographic image is mistakenly imaged using one of the radiographic imaging devices 14 other than the radiographic imaging device 14 that was to be used for imaging the radiographic image. In this case, it may be that the image ID received by the control section 30 and memorized in the memory section 32 in step S608 and the image ID received in step S614 are different.

In step S616, if the image IDs do not coincide, the control section 30 proceeds to step S618. In step S618, the memory section 32 displays a warning indicating that the radiographic imaging device 14 is incorrect. Then, in step S620, the memory section 32 changes the image ID memorized in the memory section 32 to the image ID received subsequently (in step S614), and the control section 30 proceeds to step S622. Thus, because the image ID is changed, although the radiographic imaging device 14 used for imaging is different from the expected radiographic imaging device 14, the image data, image ID and patient ID of the imaged radiographic image may be associated at the console 18.

Because of the warning display in step S618, the user may recognize that the imaging has been performed with a different radiographic imaging device 14 from the expected radiographic imaging device 14. In this case, if it is necessary to perform the imaging with the expected radiographic imaging device 14, it is sufficient for the user to change the radiographic imaging device 14 used for the imaging to the expected radiographic imaging device 14 and then repeat the imaging (the present processing) again. Alternatively, if there is no effect from using the radiographic imaging device 14 that has been used for the present imaging even though it is different from the expected radiographic imaging device 14, the present image data, image ID and patient ID of the imaged radiographic image may be associated by the console 18 in this state, and consequently there is no need to repeat the imaging.

It may be that the imaging device ID is received as well as the image ID in step S614 and a determination is made in step S616 as to whether the imaging device IDs coincide. Because a determination is made as to whether the imaging device IDs coincide, a more suitable determination may be made as to whether the expected radiographic imaging device 14 has been used for the imaging.

On the other hand, if the image IDs coincide in step S616, the control section 30 proceeds to step S622.

Then, in step S622, the control section 30 makes a determination as to whether subsequent imaging is to be performed. For example, in a case in which there is a command relating to subsequent imaging or the like, the control section 30 determines that subsequent imaging is to be performed, returns to step S600, and repeats the present processing. On the other hand, if there is no subsequent imaging, the control section 30 ends the present processing.

Meanwhile, the radiographic imaging device 14 executes the processing shown in FIG. 13. FIG. 13 shows a flowchart illustrating the flow of an example of processing that is executed by the control section 22 of each radiographic imaging device 14 according to the present exemplary embodiment. In the radiographic imaging device 14 according to the present exemplary embodiment, the control section 22 functions as respective functional sections of the present invention and executes the processing shown in FIG. 13 by executing a processing program memorized in the ROM thereof.

In step S700, the control section 22 puts the radiation detector 20 into the effective state. Then, in step S704, the control section 22 generates an image ID. In step S706, the control section 22 transmits the image ID to the handheld terminal device 16 via the input/output section 26 and the interface section 28.

Then, in step S708, the control section 22 makes a determination as to whether association information has been received from the handheld terminal device 16 via the input/output section 26 and interface section 28. The control section 22 continues to wait until the association information transmitted in step S612 of the processing at the handheld terminal device 16 described above is received. If the association information is received, the control section 22 proceeds to step S710. In step S710, imaging preparation is completed. If the association information has not been received after a predetermined duration has passed since the control section 22 transmitted the image ID to the handheld terminal device 16, the control section 22 may assume that some kind of error has occurred and perform predetermined error processing, which is processing to, for example, provide a warning to a user or the like.

Then, in step S712, the control section 22 makes a determination as to whether the radiation detector 20 has detected the radiation X. If the radiation X has not been detected, the control section 22 proceeds to step S714 and makes a determination as to whether a predetermined duration has passed. For example, if a user is performing the imaging with a different one of the radiographic imaging devices 14 as described above, the radiation X is not irradiated onto the expected radiographic imaging device 14. In this case, the radiation X is not detected at the expected radiographic imaging device 14 even in a case where the predetermined duration has passed. Therefore, if the result in step S714 is affirmative, the present processing ends. On the other hand, if the predetermined duration has not passed, the control section 22 returns to step S712 and repeats the present processing.

Alternatively, if the radiation X has been detected at step S712, the control section 22 proceeds to step S716. In step S716, the control section 22 acquires a radiographic image (i.e., image data) from the radiation detector 20.

Then, in step S718, the control section 22 associates the image data of the radiographic image with the image ID generated in step S704 and memorizes the same in the memory section 24.

Then, in step S720, the control section 22 transmits the image ID to the handheld terminal device 16 in the same manner as in step S706.

Then, in step S722, the control section 22 makes a determination as to whether subsequent imaging is to be performed. For example, in a case in which there is a command relating to subsequent imaging or the like, the control section 22 determines that subsequent imaging is to be performed, returns to step S700, and repeats the present processing. On the other hand, if there is no subsequent imaging, the control section 22 ends the present processing. After step S722, the radiographic imaging device 14 according to the present exemplary embodiment switches back from the ready state to the idle state.

Processing at the console 18 according to the present exemplary embodiment to associate the patient ID, image ID and image data and memorize the same in the memory section 52 is the same as in the exemplary embodiments described above, so is not described here.

Thus, in the radiographic imaging system 10 according to the present exemplary embodiment, in a case in which a plural number of the radiographic imaging devices 14 are put into the effective state and imaging is to be performed, an image ID is received at the handheld terminal device 16 from one of the radiographic imaging devices 14 before imaging of the radiographic image, and the handheld terminal device 16 associates a patient ID with the image ID and memorizes the same in the memory section 32. Thereafter, in a case in which one of the radiographic imaging devices 14 receives the association information transmitted from the handheld terminal device 16, the radiographic imaging device 14 images the radiographic image and associates and memorizes the image data of the radiographic image with the image ID. The radiographic imaging device 14 also transmits the image ID to the handheld terminal device 16. The handheld terminal device 16 determines whether the image ID that is received the second time coincides with the image ID memorized in the memory section 32. If the image IDs do not coincide, the handheld terminal device 16 gives a warning and changes the image ID memorized in the memory section 32 to the image ID received the second time. Thus, the handheld terminal device 16 is put into a state in which the patient ID and the image ID are suitably associated.

Thus, in the radiographic imaging system 10 according to the present exemplary embodiment, patient IDs and image data may be suitably associated at the console 18 on the basis of image IDs.

[Fourth Exemplary Embodiment]

In the radiographic imaging system 10 according to the third exemplary embodiment described above, a case is described in which the plural radiographic imaging devices 14 are put into the effective state at the same time and the plural radiographic imaging devices 14 are made capable of imaging. In contrast, in the radiographic imaging system 10 according to the present exemplary embodiment, a case is described in which only one of the radiographic imaging devices 14 is put into the effective state and made capable of imaging.

The radiographic imaging system 10 according to the present exemplary embodiment is provided with similar configurations and operations to the radiographic imaging system 10 according to each exemplary embodiment described above. Accordingly, detailed descriptions of portions that are the same will be omitted.

The configuration of the radiographic imaging system 10 is the same as that of the radiographic imaging system 10 according to the third exemplary embodiment described above except in that each radiographic imaging device 14 includes a function for detecting whether or not the radiation X is irradiated thereon even if the radiographic imaging device 14 is not performing imaging. Therefore, descriptions of the configuration of the radiographic imaging system 10 are not given. The function for detecting whether or not the radiation X is irradiated is not particularly limited; existing sensors may be used.

Operations of the handheld terminal device 16 according to the present exemplary embodiment are described.

Figure 14:
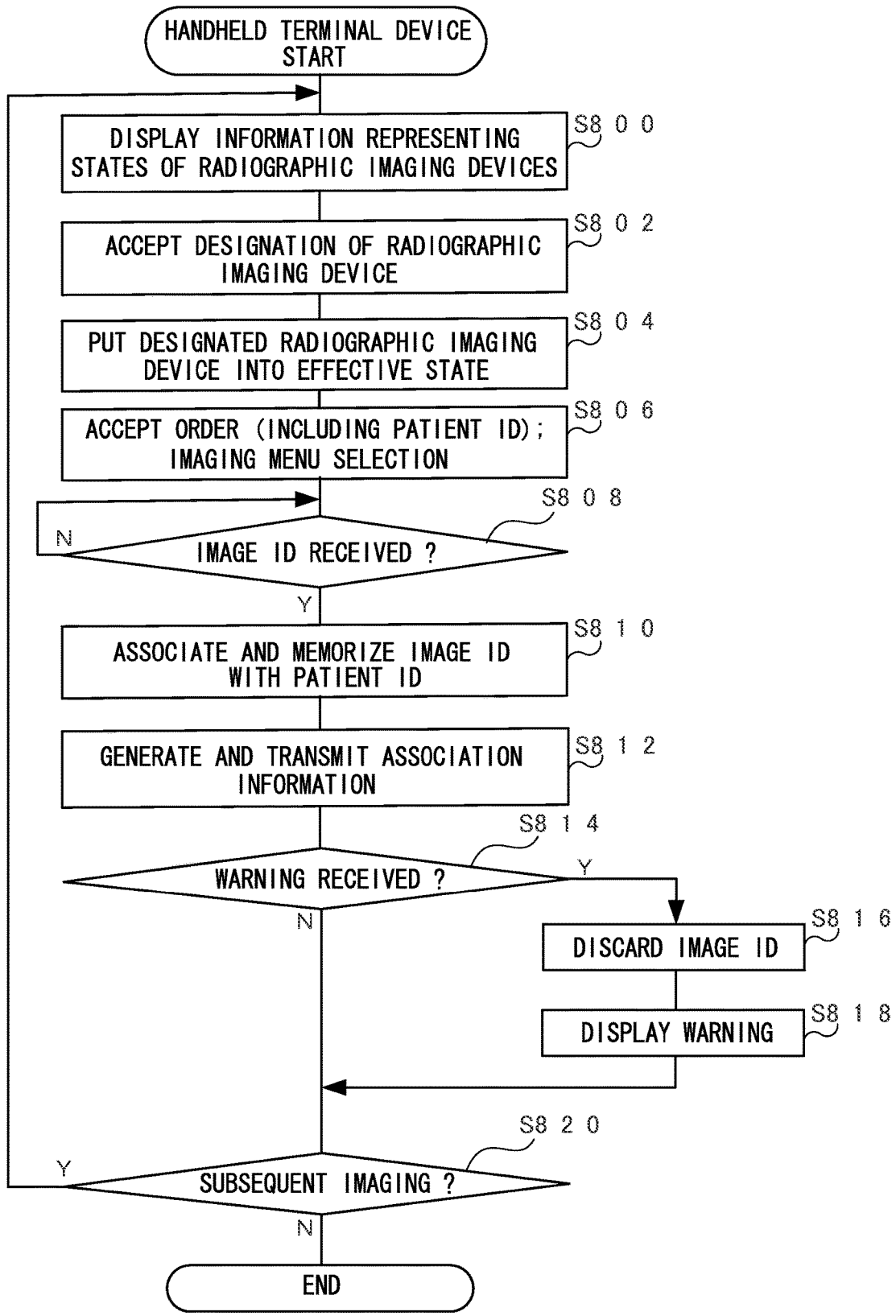
FIG. 14 is a flowchart illustrating the flow of processing of radiographic imaging relating to a handheld terminal device in accordance with a fourth exemplary embodiment.

The handheld terminal device 16 executes the processing shown in FIG. 14. FIG. 14 shows a flowchart illustrating the flow of processing that is executed by the control section 30 of the handheld terminal device 16 according to the present exemplary embodiment. In the handheld terminal device 16 according to the present exemplary embodiment, the control section 30 functions as respective functional sections of the present invention and executes the processing shown in FIG. 14 by executing a processing program memorized in the ROM thereof.

Steps S800 to S812 of the processing executed by the control section 30 of the handheld terminal device 16 according to the present exemplary embodiment are the same as steps S600 to S612 of the processing executed by the control section 30 of the handheld terminal device 16 according to the third exemplary embodiment (see FIG. 11).

In step S800, the control section 30 displays information representing states of the radiographic imaging devices 14 at the display 36. In step S802, the control section 30 accepts a designation of the radiographic imaging devices 14 that a user designates. Step S802 differs from step S602 of the third exemplary embodiment in that, in a case in which the designation is accepted in the present exemplary embodiment, only one of the radiographic imaging devices 14 is designated.

Then, in step S804, the control section 30 puts the designated radiographic imaging device 14 into the effective state. In step S806, the control section 30 accepts an order including a patient ID, and selects an imaging menu selection. In step S808, the control section 30 makes a determination as to whether an image ID has been received. If an image ID has been received, the control section 30 proceeds to step S810. In step S810, the control section 30 associates the image ID with the patient ID and memorizes the same in the memory section 32. In step S812, the control section 30 generates association information and transmits the association information to the radiographic imaging device 14.

Then, in step S814, the control section 30 makes a determination as to whether a warning has been received. In the present exemplary embodiment, in contrast to the third exemplary embodiment, only one of the radiographic imaging devices 14 is made effective and put into the ready state. Therefore, only one of the radiographic imaging devices 14 is capable of imaging. However, if a user carries out imaging with a different radiographic imaging device 14 from the radiographic imaging device 14 that is capable of imaging (the expected radiographic imaging device 14), imaging cannot be performed with this radiographic imaging device 14 and a radiographic image may not be acquired. In the present exemplary embodiment, in a case in which the radiation X is detected at the unexpected (incapable of imaging) radiographic imaging device 14, a warning is transmitted to the handheld terminal device 16. In step S814, the control section 30 makes the determination as to whether this warning has been received.

If the warning has been received, imaging has not been carried out with the expected radiographic imaging device 14 and a radiographic image has not been imaged at all. Therefore, the control section 30 proceeds to step S816 and discards the image ID (and patient ID) memorized in the memory section 32. In addition, in step S818 the control section 30 displays a warning at the display 36, and then proceeds to step S820. Because this warning is given, the user may recognize that imaging has not been properly carried out (and the radiographic image could not be acquired). Accordingly, the user may take measures such as repeating the imaging or the like.

On the other hand, if the warning has not been received, the radiographic image has been properly imaged. Therefore, the control section 30 simply proceeds to step S820.

Then, in step S820, the control section 30 makes a determination as to whether subsequent imaging is to be performed. For example, in a case in which there is a command relating to subsequent imaging or the like, the control section 30 determines that subsequent imaging is to be performed, returns to step S800, and repeats the present processing. On the other hand, if there is no subsequent imaging, the control section 30 ends the present processing.

Figure 15:
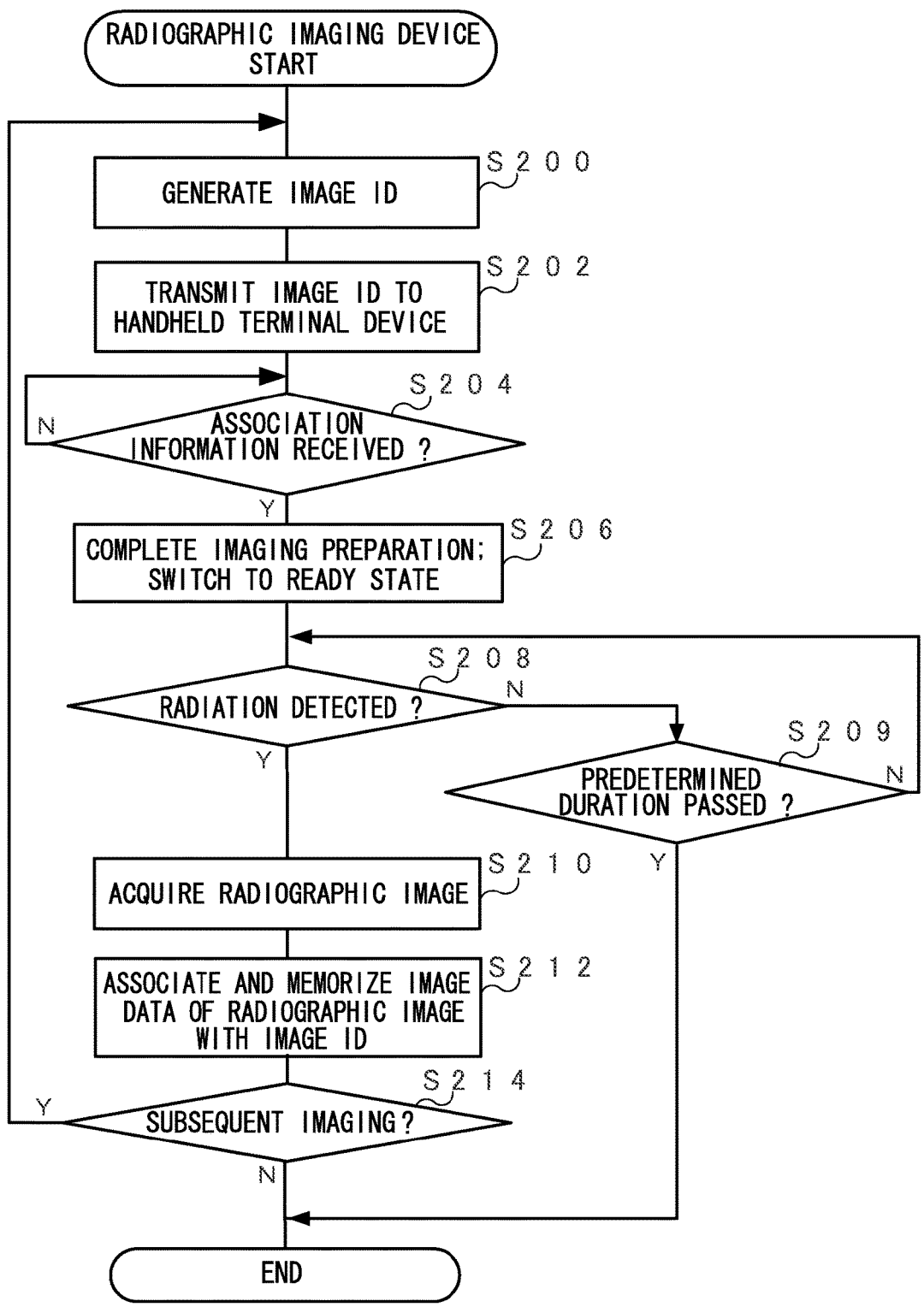
FIG. 15 is a flowchart illustrating the flow of processing of radiographic imaging relating to a radiographic imaging device in accordance with the fourth exemplary embodiment.

Meanwhile, the radiographic imaging devices 14 execute the processing shown in FIG. 15. FIG. 15 shows a flowchart illustrating the flow of an example of processing that is executed by the control section 22 of each radiographic imaging device 14 according to the present exemplary embodiment. In the radiographic imaging device 14 according to the present exemplary embodiment, the control section 22 functions as respective functional sections of the present invention and executes the processing shown in FIG. 15 by executing a processing program memorized in the ROM thereof.

The processing that is executed by the control section 22 of each radiographic imaging device 14 according to the present exemplary embodiment is similar to the processing that is executed by the control section 22 of the radiographic imaging device 14 according to the first exemplary embodiment (see FIG. 5), except that the processing is different after the determination as to whether the radiation X has been detected. Accordingly, only the processing that is different is described here.

Specifically, as shown in FIG. 15, in step S208 according to the present exemplary embodiment, the control section 22 makes the determination as to whether the radiation detector 20 has detected the radiation X, and if the radiation X has not been detected, proceeds to step S209 and makes a determination as to whether a predetermined duration has passed. This processing is the same processing as in step S714 according to the third exemplary embodiment (see FIG. 13). In the present exemplary embodiment too, as described above, the radiation X may not be detected if imaging is carried out with one of the radiographic imaging devices 14 other than the expected radiographic imaging device 14. Therefore, if the predetermined duration has passed, the result in step S209 is affirmative and the present processing ends. On the other hand, if the predetermined duration has not passed, the control section 22 returns to step S208 and repeats the present processing. Alternatively, if the radiation X has been detected at step S208, the control section 22 proceeds to step S210.

Thus, in the radiographic imaging system 10 according to the present exemplary embodiment, in a case in which a plural number of the radiographic imaging devices 14 are put into the effective state and imaging is to be performed, only one of the radiographic imaging devices 14 becomes into the effective state and is made capable of imaging. Thus, the radiographic imaging device 14 that is capable of imaging and the handheld terminal device 16 are associated in a one-to-one correspondence.

At the handheld terminal device 16, before imaging of a radiographic image, an image ID is received from the radiographic imaging device 14 and the handheld terminal device 16 associates a patient ID with the image ID and memorizes the same in the memory section 32. Hence, in a case in which the radiographic imaging device 14 receives the association information transmitted from the handheld terminal device 16, the radiographic imaging device 14 images the radiographic image, and associates and memorizes the image ID with image data of the radiographic image. If a warning from the radiographic imaging devices 14 is received at the handheld terminal device 16, the image ID is discarded and a warning is displayed. In response to this warning, the user may properly acquire the radiographic image by repeating the imaging.

Thus, in the radiographic imaging system 10 according to each of the exemplary embodiments described above, patient IDs and image data may be suitably associated at the console 18 on the basis of image IDs.

[Fifth Exemplary Embodiment]

In the radiographic imaging system 10 according to the present exemplary embodiment, a case is described in which, after the imaging of a radiographic image, the radiographic imaging device 14 creates a preview image and transmits the preview image to the handheld terminal device 16 for the user to check the imaged radiographic image.

Figure 16:
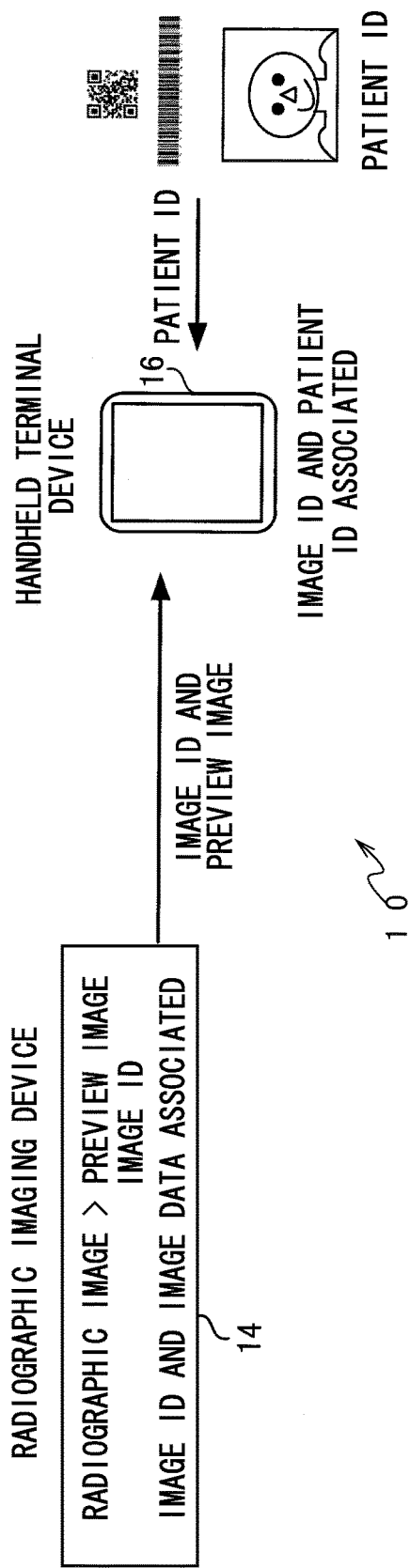
FIG. 16 is a descriptive diagram for describing a concept of associating image IDs with patient IDs in a radiographic imaging system in accordance with a fifth exemplary embodiment.

FIG. 16 is a descriptive diagram for describing a concept of associating image IDs with patient IDs in the radiographic imaging system 10 according to the present exemplary embodiment.

As illustrated in FIG. 16, in the radiographic imaging system 10 according to the present exemplary embodiment, the radiographic imaging device 14 generates an image ID after the imaging of a radiographic image. The radiographic imaging device 14 also generates a preview image based on the image data (raw data) of the radiographic image.

The term "preview image" refers to an image for a user to judge whether the imaging of a radiographic image relating to the imaging subject W has been properly carried out and at least whether a repeat of imaging is necessary, which is an image of a lower image quality than a radiographic image to be used for interpretation. The control section 22 according to the present exemplary embodiment performs image processing in order to generate the preview image from the raw data of the radiographic image, thus generating the preview image. In this case, from among plural image processes that are applied for generating a radiographic image for interpretation, the control section 22 according to the present exemplary embodiment uses image processes that require relatively short durations to generate the preview image. As a specific example, in a case of generating a radiographic image for interpretation, the control section 22 applies offset correction, gain correction and missing pixel correction to the raw data of the radiographic image, but in a case of generating a preview image, the offset correction and gain correction are applied to the raw data of the radiographic image but the missing pixel correction is not applied.

In the radiographic imaging device 14 according to the present exemplary embodiment, thinning image processing is applied to the raw data of a radiographic image as an image process for generating a preview image. Consequently, image data of the preview image has a smaller data volume than the raw data. To what level the thinning is applied may be determined in advance (in accordance with the resolution of the display 36 of the handheld terminal device 16, an image data transmission rate, the image quality of preview images required by users, and the like) or a user may designate the level of thinning from the handheld terminal device 16.

The radiographic imaging device 14 associates a generated image ID with the preview image and memorizes the same in the memory section 24, and transmits the same to the handheld terminal device 16.

Meanwhile, as shown in FIG. 16, the handheld terminal device 16 according to the present exemplary embodiment accepts a patient ID, and receives the image ID and preview image from the radiographic imaging device 14. The handheld terminal device 16 associates the image ID with the patient ID and memorizes the same in the memory section 32.

First, configurations of the radiographic imaging system 10 according to the present exemplary embodiment are described.

Figure 17:
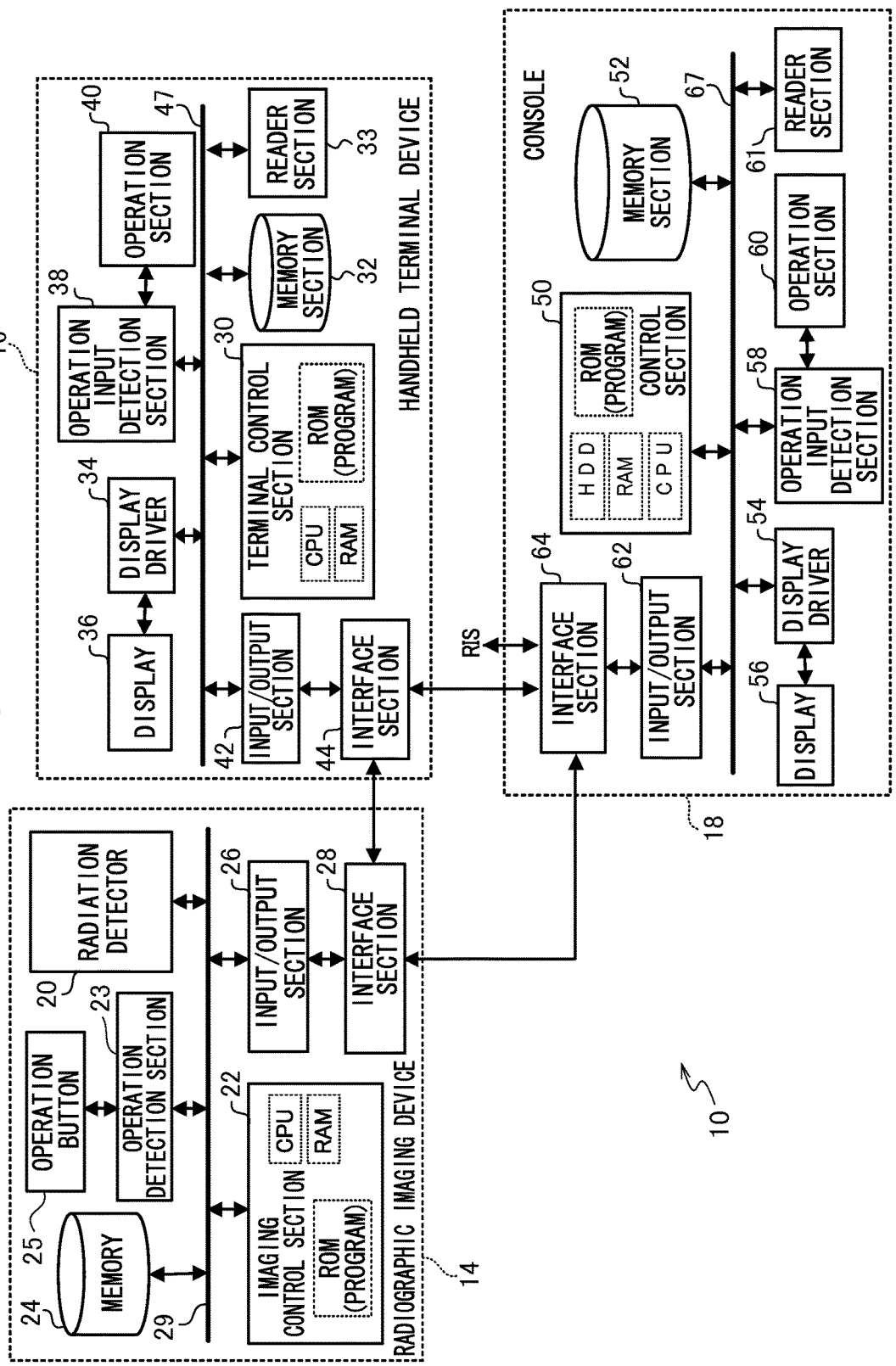
FIG. 17 is a functional block diagram showing schematic configurations of a radiographic imaging device, a handheld terminal device and a console of the radiographic imaging system in accordance with the fifth exemplary embodiment.

FIG. 17 shows a functional block diagram representing schematic configurations of examples of the radiographic imaging device 14, the handheld terminal device 16 and the console 18 of the radiographic imaging system 10 according to the present exemplary embodiment.

As shown in FIG. 17, the radiographic imaging system 10 according to the present exemplary embodiment differs from the radiographic imaging system 10 according to each of the exemplary embodiments described above (see FIG. 2) in that the handheld terminal device 16 is equipped with a reader section 33. The reader section 33 according to the present exemplary embodiment includes functions for reading text, images and the like. Specifically, the reader section 33 includes a camera function and functions as a barcode reader.

In the present exemplary embodiment, the control section 22 of the radiographic imaging device 14 functions as an example of a third generation section, and the input/output section 26 and interface section 28 function as an example of a third transmission section. The input/output section 42 and interface section 44 of the handheld terminal device 16 function as an example of a fourth reception section, and the display 36 functions as an example of a third display section.

Now, details of operations of the handheld terminal device 16 according to the present exemplary embodiment are described.

Figure 18:
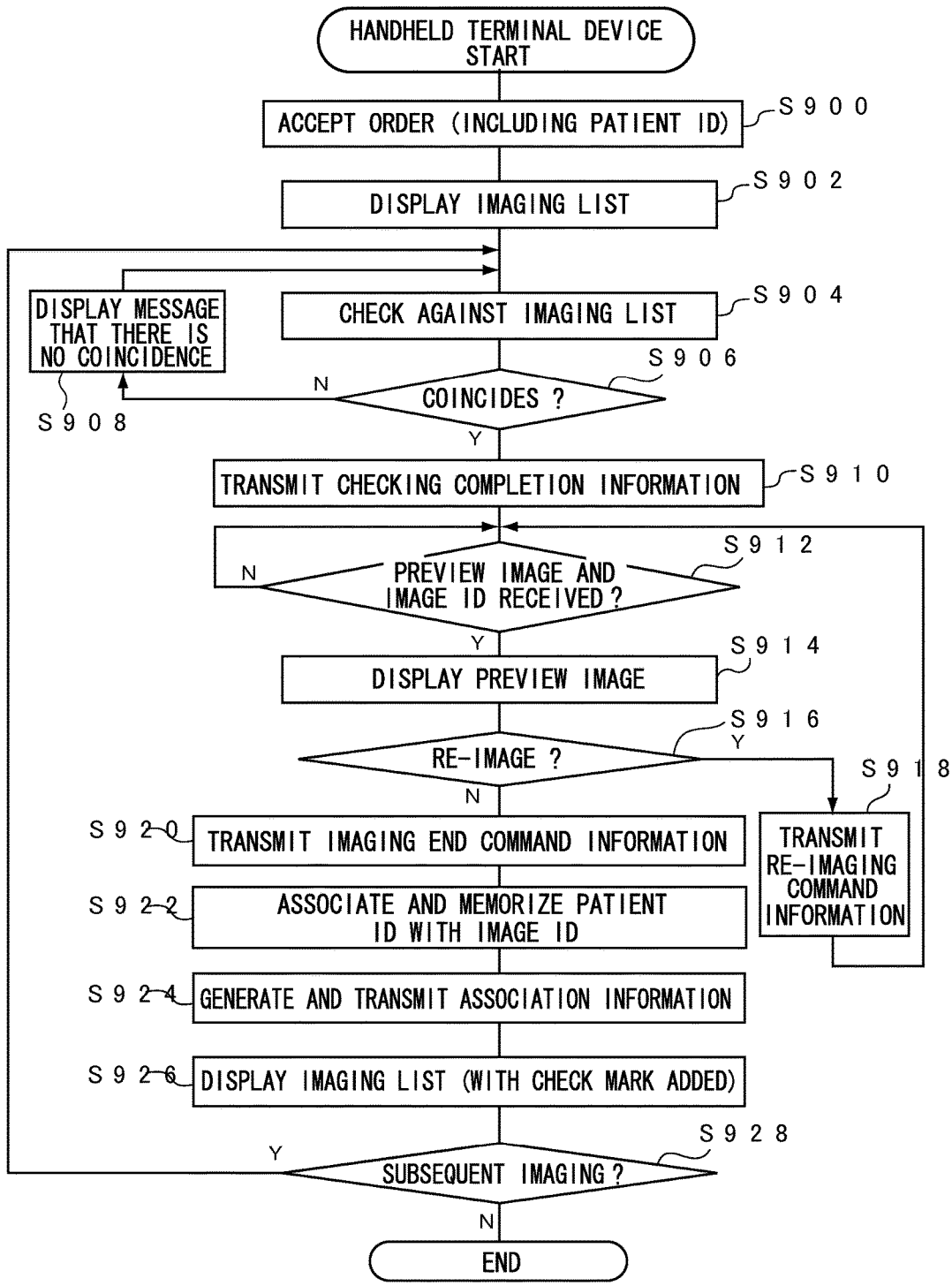
FIG. 18 is a flowchart illustrating the flow of processing that is executed by a control section of the handheld terminal device in accordance with the fifth exemplary embodiment.

The handheld terminal device 16 executes the processing illustrated in FIG. 18. FIG. 18 shows a flowchart illustrating the flow of an example of processing that is executed by the control section 30 of the handheld terminal device 16 according to the present exemplary embodiment. In the handheld terminal device 16 according to the present exemplary embodiment, the control section 30 functions as respective functional sections of the present invention and executes the processing shown in FIG. 18 by executing a processing program memorized in the ROM thereof.

In step S900 of FIG. 18, the control section 30 accepts an order including a patient ID.

In step S902, the control section 30 displays an imaging list at the display 36. The term "imaging list" in the present exemplary embodiment refers to a list of accepted orders. If plural orders have been accepted in step S900, the plural orders are included in the imaging list. Therefore, plural orders are displayed.

Figure 19:
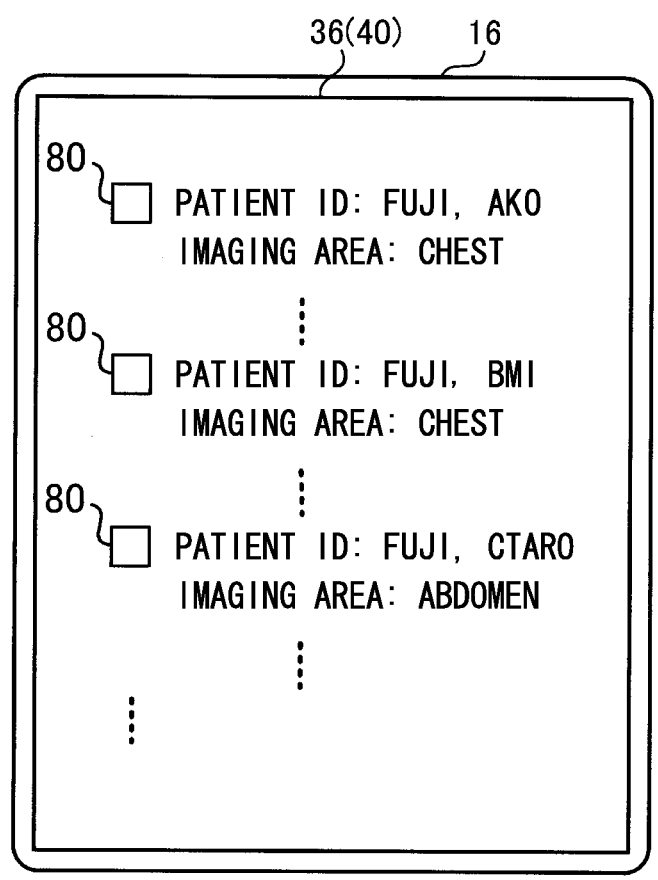
FIG. 19 is a schematic view showing a state in which an imaging list is displayed at a display of the handheld terminal device.

FIG. 19 shows a schematic view illustrating a specific example of a state in which an imaging list is displayed at the display 36 of the handheld terminal device 16. In the specific example shown in FIG. 19, plural orders are displayed as the imaging list. Respective checkboxes 80, patient IDs and orders are displayed. Each checkbox 80 represents whether or not the imaging has been completed. If there is a check mark in the checkbox 80, this indicates that the imaging has been completed.

Because the imaging list is displayed at the display 36, the user may check what imaging is to be done thereafter.

Then, in step S904, the control section 30 checks the imaging subject W. At this time, as the patient ID, the control section 30 reads, for example, the patient's name written on a name card, a medical record or the like of the imaging subject W with the reader section 33, or reads a barcode, a two-dimensional code such as a QR code (registered trademark) or such, or the like. The control section 30 checks up the imaging subject W by checking the data that is read against the information in the imaging list. As a further example, if photographic images containing the faces of the imaging subjects W are included in the information in the imaging list, the control section 30 may take a photographic image of the face of the imaging subject W with the reader section 33 and check up the imaging subject W by performing facial recognition using the face image that has been photographed. Thus, a checking method of the imaging subject W is not particularly limited. It is sufficient if the checking method is a method that may check the imaging subject W that is to be imaged against the information in the imaging list. Alternatively, fingerprint recognition or the like may be used.

Then, in step S906, the control section 30 makes a determination as to whether the imaging subject W that is the result of checking by the processing of step S904 coincides with an imaging subject W included in the orders in the imaging list. Thus, in the handheld terminal device 16 according to the present exemplary embodiment, imaging of a radiographic image of an imaging subject W who is not intended to be imaged may be inhibited by the checking of the imaging subject W.

If the imaging subject W does not coincide with the information in the imaging list, the control section 30 proceeds to step S908 and displays an indication at the display 36 that the imaging subject W does not match up. In response to the indication displayed at the display 36 that the imaging subject W does not coincide with the information in the imaging list, the user verifies that the imaging subject W is not in the imaging list. Then the user can alter the imaging of the radiographic image to an expected imaging subject W that is in the imaging list and cause the handheld terminal device 16 to check against the altered imaging subject W.

Therefore, if an imaging subject W does not coincide, the control section 30 returns to step S904 and repeats the checking of the imaging subject W.

On the other hand, if the imaging subject W coincides with the information in the imaging list, the control section 30 proceeds to step S910. In step S910, the control section 30 transmits checking completion information to the radiographic imaging device 14. In the present exemplary embodiment, the checking completion information includes information indicating that the checking of the imaging subject W has been completed and information for commanding the imaging of a radiographic image at the radiographic imaging device 14. Accordingly, in a case in which the radiographic imaging device 14 receives the checking completion information from the handheld terminal device 16, the radiographic imaging device 14 determines to start the imaging of the radiographic image (see step S1000 in FIG. 22).

Figure 22:
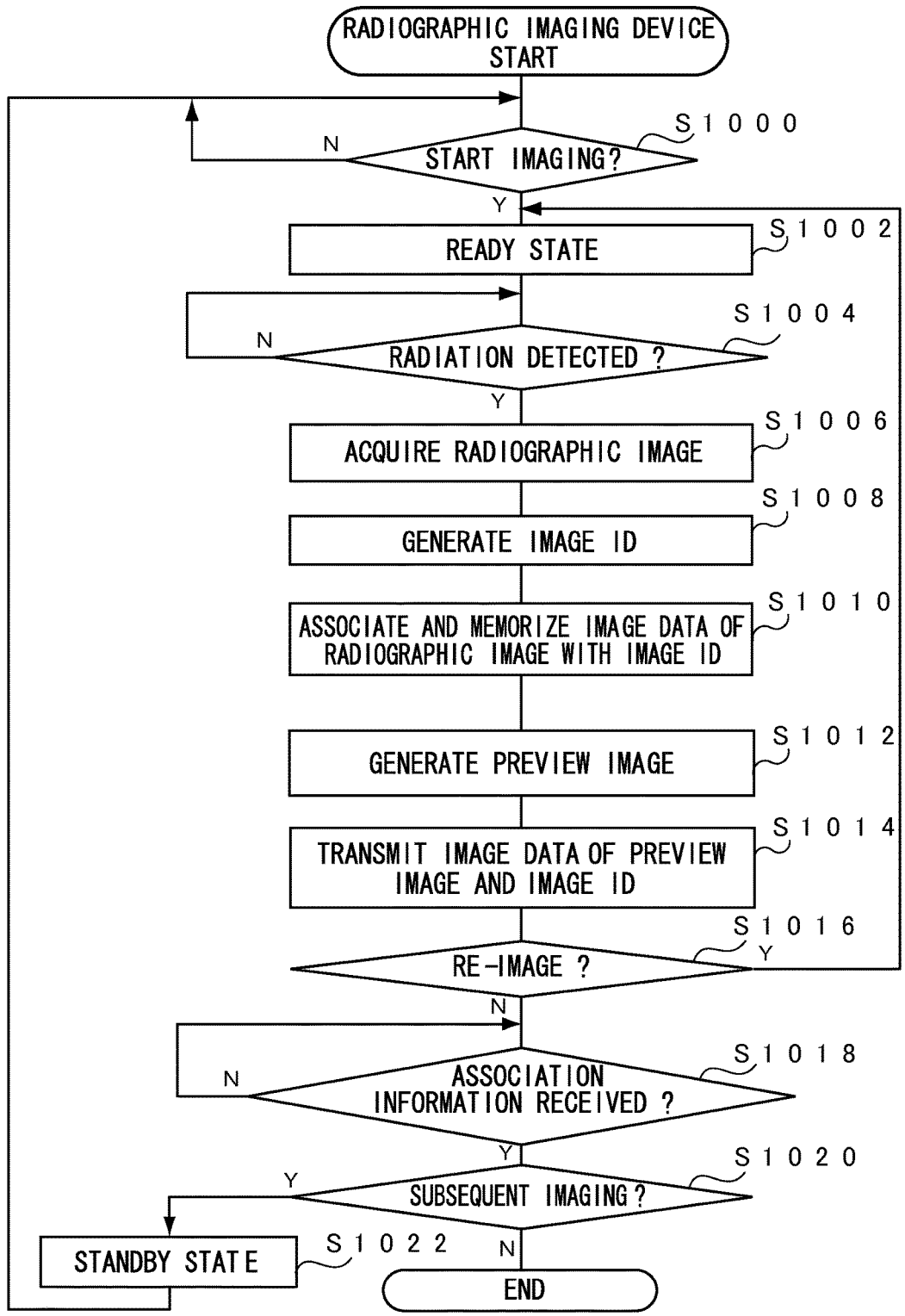
FIG. 22 is a flowchart illustrating the flow of processing that is executed by a control section in accordance with the fifth exemplary embodiment.

The radiographic imaging device 14 images the radiographic image and transmits image data representing the preview image, which is generated on the basis of the radiographic image obtained by the imaging, to the handheld terminal device 16 (see step S1014 in FIG. 22).

Therefore, in step S912, the control section 30 makes a determination as to whether an image ID and image data of a preview image have been received. Specifically, the control section 30 makes a determination as to whether an image ID and image data of the preview image of the radiographic image to which that image ID is assigned have been received. The control section 30 waits until the same are received and, in case they are received, the control section 30 proceeds to step S914.

Figure 20:
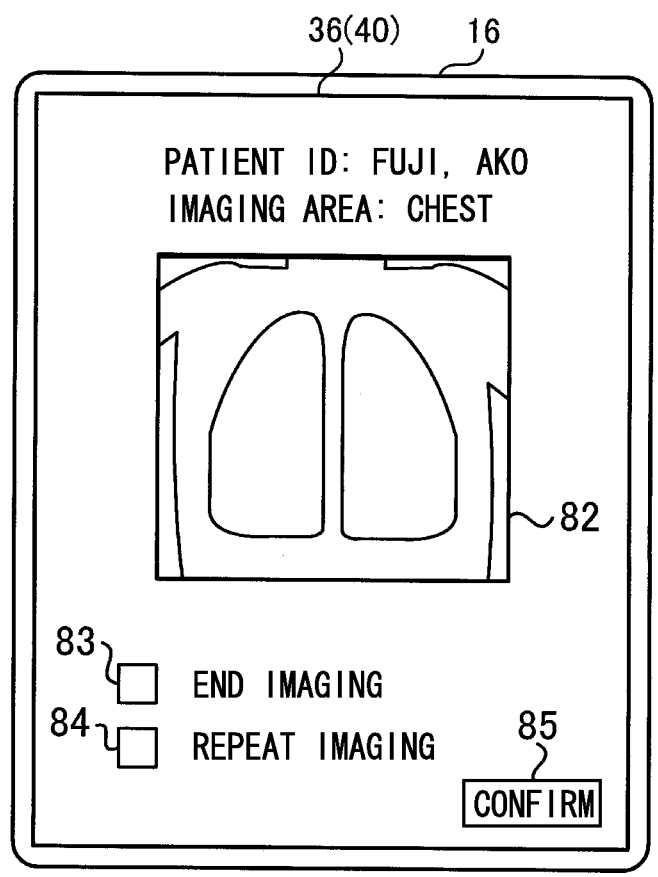
FIG. 20 is a schematic view showing a state in which a preview image is displayed at the display of the handheld terminal device.

In step S914, the control section 30 displays the received preview image at the display 36. FIG. 20 is a schematic view showing a specific example of a state in which a preview image 82 is displayed at the display 36 of the handheld terminal device 16.

The user checks the preview image 82 and determines whether or not to repeat imaging. The user commands re-imaging if the radiographic image obtained by the imaging is not suitable, due to a target region not being included in the displayed preview image 82, blur, shake or the like occurring in the image, or the like. The radiographic imaging device 14 according to the present exemplary embodiment detects the start of an irradiation of the radiation X at the radiographic imaging device 14 and images the radiographic image without synchronization with the radiation irradiation device 12. Therefore, it may be that, because of noise from an impact against the radiographic imaging device 14 or the like, the start of an irradiation of the radiation X is falsely detected, a radiographic image is imaged and a preview image thereof is transmitted to the handheld terminal device 16. In such a case, the user will command re-imaging.

Specifically, in the handheld terminal device 16 according to the present exemplary embodiment, if a user is commanding re-imaging, the user performs an operation to insert a check mark in a checkbox 84 displayed at the display 36, and then operates a confirm button 85.

On the other hand, if re-imaging is not to be performed but imaging is to be ended, the user performs an operation to insert a check mark in a checkbox 83 displayed at the display 36, and then operates the confirm button 85.

The control section 30 detects these operations with the operation input detection section 38. Then, if the control section 30 detects that the command operation to repeat imaging has been given by the user, the control section 30 proceeds to step S918, transmits re-imaging command information to the radiographic imaging device 14, and then returns to step S912.

On the other hand, if the control section 30 detects that the command operation to end imaging has been given by the user, the control section 30 proceeds to step S920. In step S920, the control section 30 transmits imaging end command information to the radiographic imaging device 14, and then proceeds to step S922.

In step S922, the control section 30 associates the patient ID with the image ID that was received in a case in which the result of the determination in step S912 was affirmative, and memorizes the patient ID and image ID in the memory section 32.

Then, in step S924, the control section 30 generates association information and transmits the same to the radiographic imaging device 14, in the same manner as in step S412 of the processing executed by the control section 30 of the handheld terminal device 16 according to the second exemplary embodiment described above (see FIG. 8).

Figure 21:
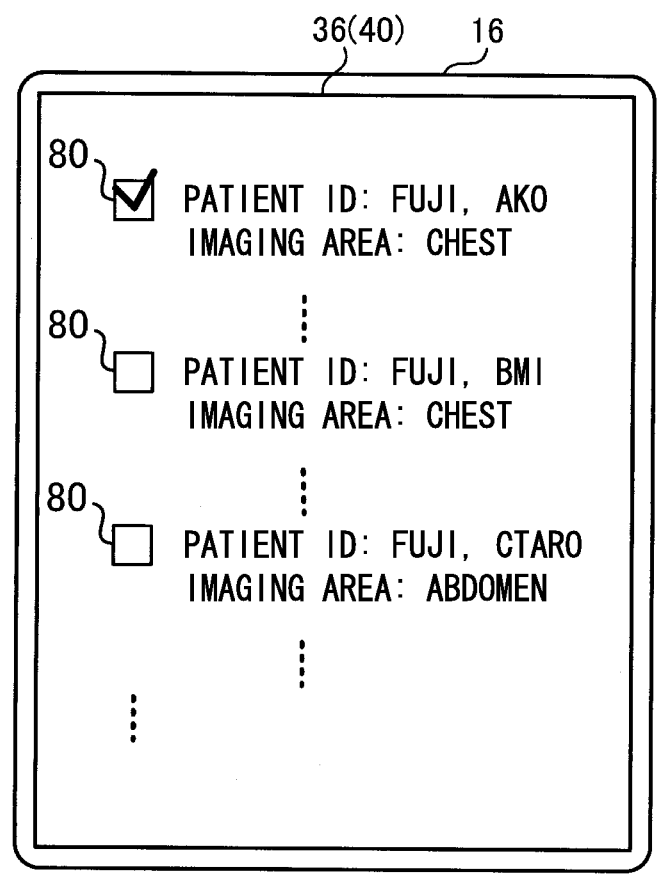
FIG. 21 is a schematic view showing a state in which an imaging list including a completed imaging order is displayed at the display of the handheld terminal device.

Then, in step S926, the control section 30 again displays the imaging list at the display 36. At this time, the control section 30 displays a state in which a check mark is inserted in the checkbox 80 corresponding to the order for which imaging has ended. FIG. 21 shows a schematic view illustrating a specific example of a state in which an imaging list including an order whose imaging has been completed is displayed at the display 36 of the handheld terminal device 16. In the specific example shown in FIG. 21, a check mark is inserted in the checkbox 80 corresponding to the record displayed at the top: "Patient ID: Fuji, Ako, Imaging area: Chest", etc., indicating that the imaging corresponding to this information has ended. The user may check whether or not there is an order for which imaging of a radiographic image has not yet been completed from whether or not there is a check mark in each checkbox 80.

The imaging of radiographic images is not limited by the order of listing in the imaging list. The imaging is conducted in an order according to the completion of checking by the processing of steps S904 to S910.

Then, in step S928, the control section 30 makes a determination as to whether subsequent imaging is to be performed. Specifically, the control section 30 makes a determination as to whether imaging corresponding to all of the orders contained in the imaging list has been completed. If the control section 30 determines that the same has not been completed, the control section 30 returns to step S904 and repeats the present processing. On the other hand, if there is no subsequent imaging, the control section 30 ends the present processing.

Meanwhile, the radiographic imaging device 14 executes the processing shown in FIG. 22. FIG. 22 shows a flowchart illustrating the flow of an example of processing that is executed by the control section 22 according to the present exemplary embodiment. In the radiographic imaging device 14 according to the present exemplary embodiment, the control section 22 functions as respective functional sections of the present invention and executes the processing shown in FIG. 22 by executing a processing program memorized in the ROM thereof.

In step S1000 of FIG. 22, the control section 22 makes a determination as to whether imaging of a radiographic image is to start. Specifically, if checking completion information has been received from the handheld terminal device 16 (see step S910 of FIG. 18), the control section 22 determines that imaging of a radiographic image is to start.

If the checking completion information has not been received, the control section 22 continues to wait, and if the checking completion information has been received, the control section 22 proceeds to step S1002.

In step S1002, the control section 22 performs control to switch the radiation detector 20 into the ready state, which is the state in which the start of an irradiation of the radiation X can be detected immediately. In the ready state, the radiation detector 20 performs operations for detecting the start of an irradiation of the radiation X or the like. Therefore, power consumption amounts are greater than in a standby state (described in detail below; see step S1020).

Then, in step S1004, the control section 22 makes a determination as to whether the radiation detector 20 has detected the radiation X. The control section 22 continues in the ready state until the radiation X is detected. If the radiation X has been detected, the control section 22 proceeds to step S1006.

In step S1006, the control section 22 acquires a radiographic image (image data) from the radiation detector 20.

Then, in step S1008, the control section 22 generates an image ID. In step S1010, the control section 22 associates the image data of the radiographic image with the image ID generated in step S1008 and memorizes the same in the memory section 24.

Then, in step S1012, the control section 22 generates a preview image as described above on the basis of the image data (the raw data) memorized in the memory section 24.

Then, in step S1014, the control section 22 transmits the generated image data of the preview image and the image ID of the radiographic image corresponding to the preview image to the handheld terminal device 16. At the handheld terminal device 16, the preview image is displayed at the display 36 on the basis of the received image data (see step S914 of FIG. 18).

As described above, having checked the preview image 82 displayed at the display 36 of the handheld terminal device 16 (see FIG. 20), the user commands re-imaging or the end of imaging.

Then, in step S1016, the control section 22 makes a determination as to whether the imaging is to be repeated, on the basis of a determination as to whether re-imaging command information has been received from the handheld terminal device 16. If the result of this determination is affirmative, the control section 22 returns to step S1002 and repeats the imaging of the radiographic image of the imaging subject W. In a case in which imaging is repeated, it is preferable if information indicating that the imaging is repeated is associated with the image data of the radiographic image for which re-imaging has been commanded as a result of the user checking the preview image, and this information and image data are memorized in the memory section 24.

On the other hand, if the result of the determination in step S1016 is negative, the control section 22 understands that the imaging end command information has been received from the handheld terminal device 16 and proceeds to step S1018.

If imaging of a plural number of radiographic images is commanded in a single order, such as imaging of plural radiographic images of the same imaging subject W or the like, the processing of steps S1002 to S1016 is repeated.

After the end of the imaging of the radiographic image, the handheld terminal device 16 associates the patient ID with the image ID and memorizes the same in the memory section 32, and transmits the association information to the radiographic imaging device 14 (see step S924 of FIG. 18).

In step S1018, the control section 22 makes a determination as to whether the association information has been received. If the association information has not yet been received, the control section 22 continues to wait, and if the association information has been received, the control section 22 proceeds to step S1020.

Then, in step S1020, the control section 22 makes a determination as to whether subsequent imaging is to be performed. If there is subsequent imaging, the control section 30 proceeds to step S1022, and performs control to put the radiation detector 20 into the standby state. The term "standby state" according to the present exemplary embodiment refers to a state in which a power supply switch of the radiographic imaging device 14 is turned on and the radiographic imaging device 14 is waiting for imaging of a radiographic image to be commanded. On the other hand, if there is no subsequent imaging, the control section 22 ends the present processing.

[Sixth Exemplary Embodiment]

In the radiographic imaging system 10 according to the fifth exemplary embodiment described above, the radiographic imaging device 14 generates a preview image of every radiographic image that is imaged and transmits the preview image to the handheld terminal device 16, and the preview image of every radiographic image is displayed at the display 36 of the handheld terminal device 16. In contrast, in the radiographic imaging system 10 according to the present exemplary embodiment, a case is described in which, only if the radiographic imaging device 14 determines that the radiation X has been falsely detected does the radiographic imaging device 14 generate a preview image of the radiographic image obtained by the false detection and transmit the preview image to the handheld terminal device 16, and the preview image is displayed at the display 36 of the handheld terminal device 16.

The radiographic imaging system 10 according to the present exemplary embodiment is provided with similar configurations and operations to the radiographic imaging system 10 according to the fifth exemplary embodiment described above. Accordingly, detailed descriptions of portions that are the same are not given. In the present exemplary embodiment, the control section 22 of the radiographic imaging device 14 functions as an example of a determination section.

First, operations of the handheld terminal device 16 according to the present exemplary embodiment are described in detail.

Figure 23:
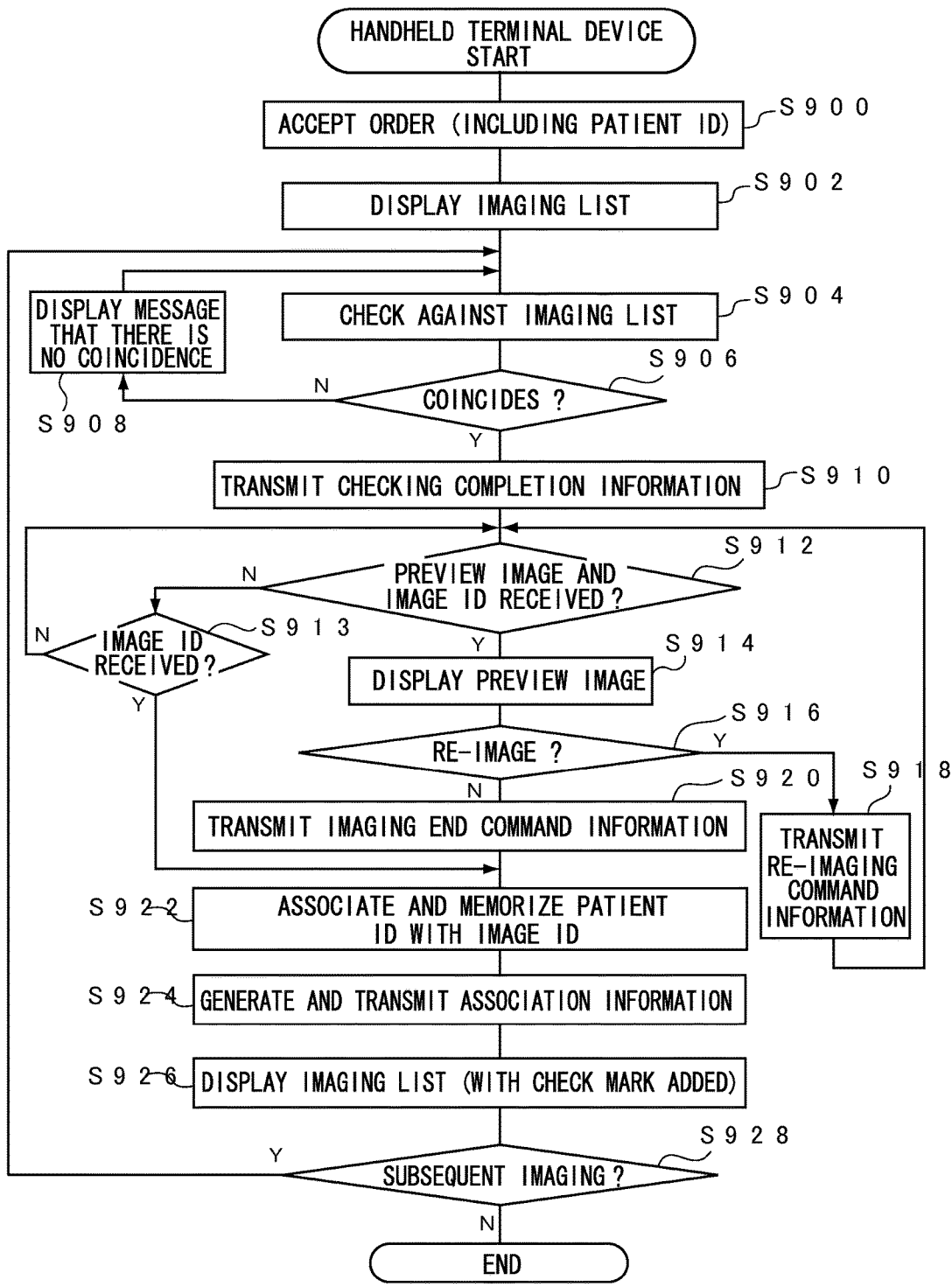
FIG. 23 is a flowchart illustrating the flow of processing that is executed by a control section of a handheld terminal device in accordance with a sixth exemplary embodiment.

The handheld terminal device 16 executes the processing shown in FIG. 23. FIG. 23 shows a flowchart illustrating the flow of processing that is executed by the control section 30 of the handheld terminal device 16 according to the present exemplary embodiment. In the handheld terminal device 16 according to the present exemplary embodiment, the control section 30 functions as respective functional sections of the present invention and executes the processing shown in FIG. 23 by executing a processing program memorized in the ROM thereof.

As shown in FIG. 23, the processing that is executed by the control section 30 of the handheld terminal device 16 according to the present exemplary embodiment is similar to the processing that is executed by the control section 30 of the handheld terminal device 16 according to the fifth exemplary embodiment (see FIG. 18), except that the processing is different after a negative result of the determination in step S912. Accordingly, only the processing that is different is described here.

As shown in FIG. 23, in the handheld terminal device 16 according to the present exemplary embodiment, if image data of a preview image and an image ID have not been received at step S912, the result of the determination is affirmative and the control section 30 proceeds to step S913.

As mentioned above, in a case in which it is determined that the radiation X has been falsely detected at the radiographic imaging device 14 according to the present exemplary embodiment, a preview image of the radiographic image obtained by the false detection is generated and transmitted to the handheld terminal device 16. Alternatively, if it is determined that the radiation X has not been falsely detected, the radiographic imaging device 14 does not generate a preview image. Therefore, if it is determined that the radiographic imaging device 14 has not falsely detected the radiation X, that is, if proper imaging of the radiographic image has been implemented, the handheld terminal device 16 does not receive image data of a preview image from the radiographic imaging device 14 but receives only the image ID.

Therefore, in step S913 the control section 30 makes a determination as to whether an image ID has been received from the radiographic imaging device 14. If no image ID has been received, the control section 30 returns to step S912.

On the other hand, if an image ID has been received, the control section 30 proceeds to step S922.

In the handheld terminal device 16 according to the present exemplary embodiment, the preview image that is displayed in step S914 after the result of the determination in step S912 is affirmative is a preview image of a radiographic image obtained by a false detection of the radiation X.

Figure 24:
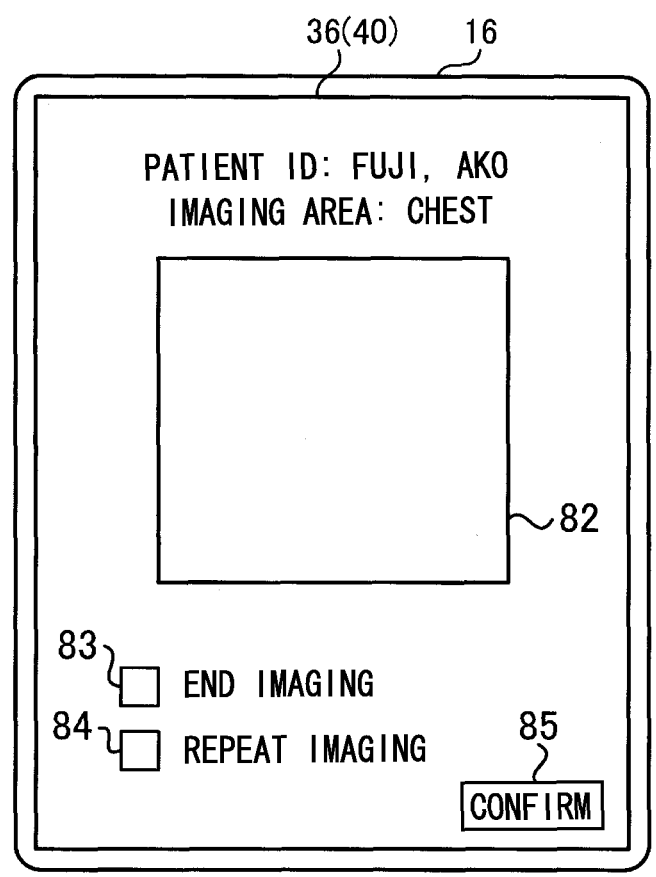
FIG. 24 is a schematic view showing a state in which a preview image is displayed at a display of the handheld terminal device in a case in which radiation has been falsely detected.

FIG. 24 is a schematic view showing a specific example of a state in which the preview image 82 is displayed at the display 36 of the handheld terminal device 16 in this situation. If the radiographic imaging device 14 has falsely detected the radiation X and carried out imaging even though radiation X required for imaging of a radiographic image has not been irradiated, the radiographic image obtained by this imaging is often a white image (an entirely plain white image). FIG. 24 illustrates a case in which the preview image is a white image, as a specific example.

The user checks the preview image 82 and determines whether or not to repeat imaging. If the displayed preview image 82 is the white image illustrated in FIG. 24 or the like and the user determines that the preview image 82 has been imaged by a false detection of the radiation X, then in order to command re-imaging, the user performs an operation to insert a check mark in the checkbox 84 displayed at the display 36 and subsequently operates the confirm button 85.

On the other hand, if the user decides that the radiographic image has been suitably imaged even though the radiographic imaging device 14 has determined that the detection was a false detection, then in order to end imaging without re-imaging, the user performs an operation to insert a check mark in the checkbox 83 displayed at the display 36 and subsequently operates the confirm button 85.

Figure 25:
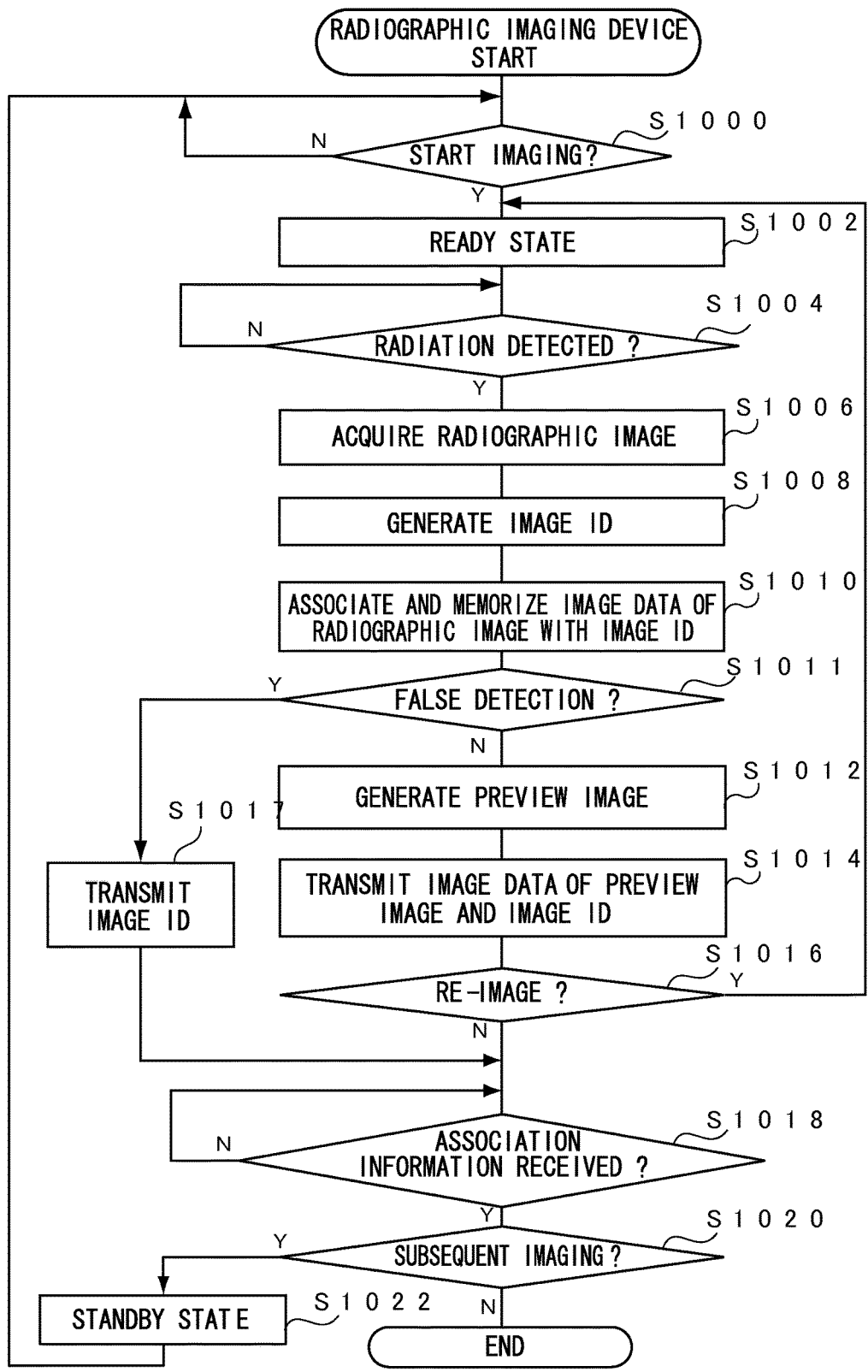
FIG. 25 is a flowchart illustrating the flow of processing that is executed by a control section in accordance with the sixth exemplary embodiment.

Now, operations of the radiographic imaging device 14 according to the present exemplary embodiment are described in detail. The radiographic imaging device 14 according to the present exemplary embodiment executes the processing shown in FIG. 25. FIG. 25 shows a flowchart illustrating the flow of an example of processing that is executed by the control section 22 of the radiographic imaging device 14 according to the present exemplary embodiment. In the radiographic imaging device 14 according to the present exemplary embodiment, the control section 22 functions as respective functional sections of the present invention and executes the processing shown in FIG. 25 by executing a processing program memorized in the ROM thereof.

As shown in FIG. 25, the processing that is executed by the control section 22 of the radiographic imaging device 14 according to the present exemplary embodiment is similar to the processing that is executed by the control section 22 of the radiographic imaging device 14 according to the fifth exemplary embodiment (see FIG. 22), except that the processing of step S1011 and the processing of step S1017 are different after step S1010. Accordingly, only the processing that is different is described here.

As shown in FIG. 25, in the radiographic imaging device 14 according to the present exemplary embodiments, after step S1010, the control section 22 proceeds to step S1011.

In step S1011, the control section 22 makes a determination as to whether the radiation detector 20 has falsely detected the radiation X, similarly to step S520 of the second exemplary embodiment described above. If the control section 22 determines that the radiation X has been falsely detected, the result of the determination is affirmative and the control section 22 proceeds to step S1012.

On the other hand, if the control section 22 determines that the detection is not a false detection, the result of the determination is negative and the control section 22 proceeds to step S1017.

In step S1017, the control section 22 transmits the image ID generated in step S1008 to the handheld terminal device 16, and then proceeds to step S1018.

Thus, in the radiographic imaging device 14 according to the present exemplary embodiment, if it is determined that the radiation X has not been falsely detected, that is, if it is determined that proper imaging of a radiographic image has been carried out, the preview image is not generated and only the generated image ID is transmitted to the handheld terminal device 16. Therefore, time required for the generation of a preview image may be saved in this case.

At the radiographic imaging device 14 according to the present exemplary embodiment, the image data of a radiographic image obtained by a false detection of the radiation X is associated with the image ID and memorized in the memory section 24. At the handheld terminal device 16, the image data of a radiographic image obtained by a false detection of the radiation X is associated with the patient ID and memorized in the memory section 32. Therefore, at the radiographic imaging device 14, it is preferable to further associate information indicating that the processing of step S1011 determined that the detection was a false detection, information indicating that re-imaging was commanded from the handheld terminal device 16 and the like with the image ID and memorize the same in the memory section 24.

[Seventh Exemplary Embodiment]

In the radiographic imaging system 10 according to the sixth exemplary embodiment described above, if the radiographic imaging device 14 determines that the radiation X has been falsely detected, the radiographic imaging device 14 generates a preview image of the radiographic image obtained by the false detection and transmits the preview image to the handheld terminal device 16, and the preview image is displayed at the display 36 of the handheld terminal device 16. In contrast, for the radiographic imaging system 10 according to the present exemplary embodiment, a case is described in which, only if it is determined that the radiation X has not been falsely detected does the radiographic imaging device 14 generate a preview image of an imaged radiographic image and transmit the preview image to the handheld terminal device 16, and the preview image is displayed at the display 36 of the handheld terminal device 16.

The radiographic imaging system 10 according to the present exemplary embodiment is provided with similar configurations and operations to the radiographic imaging system 10 according to the fifth exemplary embodiment described above. Accordingly, detailed descriptions of portions that are the same are not given. In the present exemplary embodiment, the control section 22 of the radiographic imaging device 14 functions as an example of the determination section.

First, operations of the handheld terminal device 16 according to the present exemplary embodiment are described in detail. The processing that is executed by the control section 30 of the handheld terminal device 16 according to the present exemplary embodiment is the same as the processing executed by the control section 30 of the handheld terminal device 16 according to the fourth exemplary embodiment (see FIG. 18).

As mentioned above, in a case in which it is determined that the radiation X has not been falsely detected at the radiographic imaging device 14 according to the present exemplary embodiment, a preview image of the imaged radiographic image is generated and transmitted to the handheld terminal device 16. Alternatively, if it is determined that the radiation X has been falsely detected, image data of the radiographic image and the image ID are not transmitted to the handheld terminal device 16 (see FIG. 26).

Therefore, in the handheld terminal device 16 according to the present exemplary embodiment, the image ID is received from the radiographic imaging device 14 and the result of the determination in step S912 shown in FIG. 18 is affirmative only if the radiographic imaging device 14 determines that the radiation X has not been falsely detected.

Cases in which the radiographic imaging device 14 determines that the radiation X has not been falsely detected may include cases in which the radiographic image is not suitable.

Such cases include cases in which the radiographic image obtained by the imaging is not suitable because, for example, as mentioned above, a target region is not included in the imaged radiographic image, blur, shake or the like occurs in the image, or the like. As a further example, there may be cases in which noise or the like is caused by an impact or the like during the imaging of the radiographic image. As still another example, there may be cases in which the radiation is actually falsely detected but the radiographic imaging device 14 determines that the radiation X has not been falsely detected.

Correspondingly, if the radiographic imaging device 14 determines that the radiation X has not been falsely detected, the handheld terminal device 16 according to the present exemplary embodiment receives the image data of the preview image and the image ID and displays the preview image at the display 36 (step S914), and the preview image may be checked by a user.

Hence, the user may command re-imaging if the radiographic image is not suitable.

Figure 26:
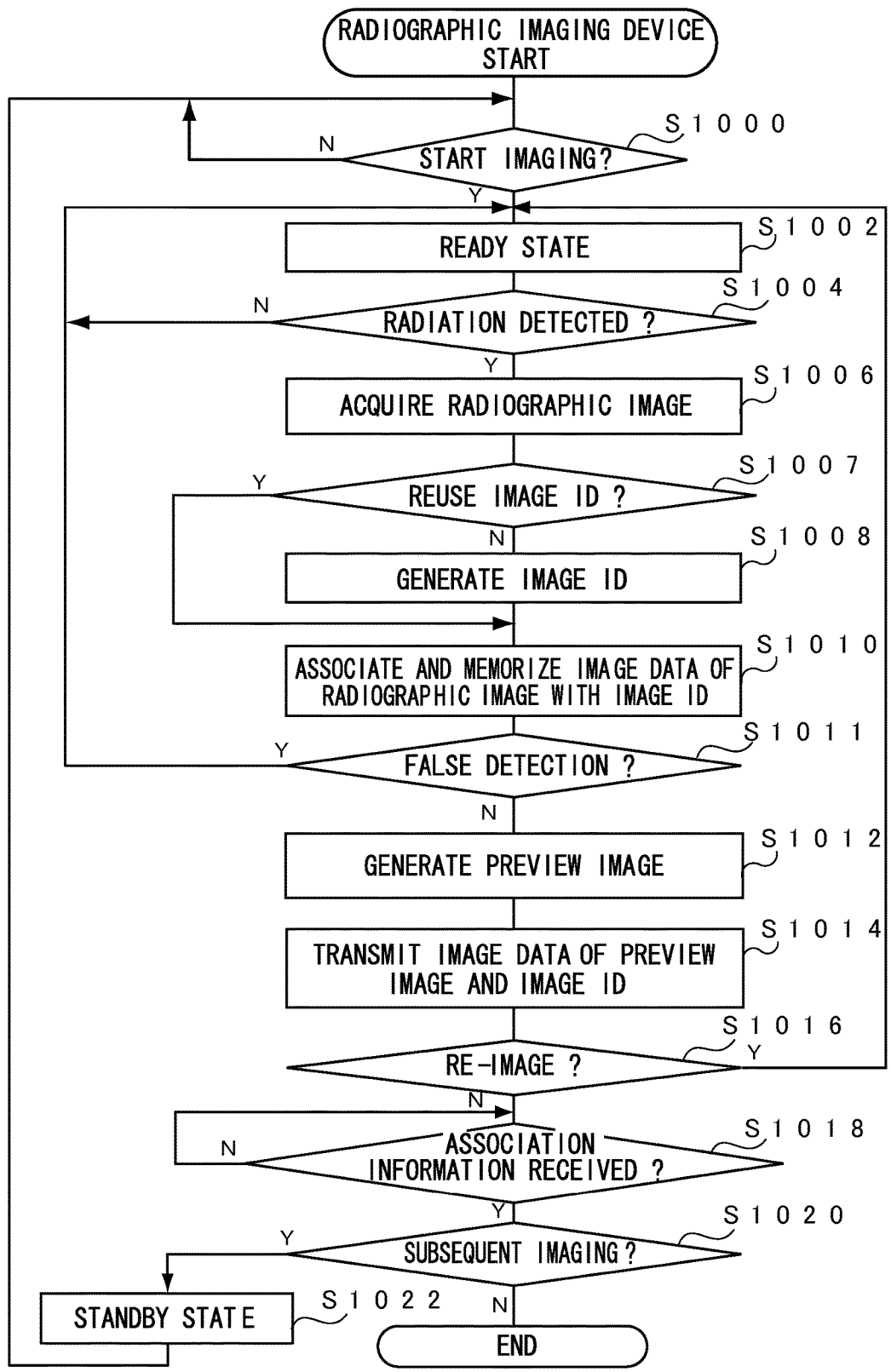
FIG. 26 is a flowchart illustrating the flow of processing that is executed by a control section of a radiographic imaging device in accordance with a seventh exemplary embodiment.

Now, operations of the radiographic imaging device 14 according to the present exemplary embodiment are described in detail. The radiographic imaging device 14 according to the present exemplary embodiment executes the processing shown in FIG. 26. FIG. 26 shows a flowchart illustrating the flow of an example of processing that is executed by the control section 22 of the radiographic imaging device 14 according to the present exemplary embodiment. In the radiographic imaging device 14 according to the present exemplary embodiment, the control section 22 functions as respective functional sections of the present invention and executes the processing shown in FIG. 26 by executing a processing program memorized in the ROM thereof.

As shown in FIG. 26, the processing that is executed by the control section 22 of the radiographic imaging device 14 according to the present exemplary embodiment is similar to the processing that is executed by the control section 22 of the radiographic imaging device 14 according to the fifth exemplary embodiment (see FIG. 22), except that the processing of step S1007 is executed after step S1006, and if the result of the determination in step S1011 is negative, the control section 22 proceeds to step S1004. Accordingly, only the processing that is different is described here.

As shown in FIG. 26, in the radiographic imaging device 14 according to the present exemplary embodiment, after step S1006, the control section 22 proceeds to step S1007.

If the result of the determination in step S1011, which is described below, is affirmative and the control section 22 returns to step S1004, an image ID has already been generated by the processing of step S1008. Image data of a suitable radiographic image has not been associated with this image ID. Therefore, if the image data of the radiographic image obtained by the false detection of the radiation X is discarded or the like, this image ID may be reused as an image ID to be associated with image data of a radiographic image that is subsequently imaged.

Therefore, in step S1007, the control section 22 makes a determination as to whether to generate an image ID. If an image ID is not to be reused, the control section 22 proceeds to step S1008 and creates a new image ID. On the other hand, if an image ID is to be reused, the control section 22 proceeds to step S1010. The method of determining whether or not to reuse an image ID is not particularly limited. For example, it may be determined that an image ID is to be reused if step S1007 is being executed after a negative result of the determination in step S1011. As another example, the determination may be based on specification by a user.

Meanwhile, if the result of the determination in step S1007 is affirmative, the control section 22 proceeds to step S1010. In this case, in step S1010 the reused image ID is associated with the image data of a radiographic image obtained in step S1006 and memorized in the memory section 24. In this situation, the same image ID has already been associated with the image data of a radiographic image obtained by a false detection of the radiation X and memorized in the memory section 24. Therefore, the control section 22 according to the present exemplary embodiment deletes the matching image ID and the image data of the previous radiographic image associated with that image ID from the memory section 24, and the control section 22 associates the reused image ID with the image data of the new radiographic image and memorizes the same in the memory section 24. Thus, duplication of the same image ID in the memory section 24 is inhibited.

As described above, in the radiographic imaging system 10 according to each of the above exemplary embodiments, if a radiographic image is imaged without using the console 18, the radiographic imaging device 14 generates an image ID and transmits the image ID to the handheld terminal device 16. The handheld terminal device 16 associates the received image ID with a patient ID and memorizes the same in the memory section 32, and the radiographic imaging device 14 associates image data of an imaged radiographic image with the image ID and memorizes the same in the memory section 24. After imaging is completed, separately, the console 18 receives the associated image ID and patient ID from the handheld terminal device 16, and the console 18 receives the associated image ID and image data from the radiographic imaging device 14.

Thus, in the radiographic imaging system 10 according to the present exemplary embodiments, the patient ID and image data may be properly associated at the console 18 on the basis of the image ID. Thus, convenience for users in a case in which the handheld terminal device 16 is used to image radiographic images may be improved.

Furthermore, in the radiographic imaging system 10 according to each of the exemplary embodiments described above, in a case in which a radiographic image is imaged, the image ID and association information are communicated between the radiographic imaging device 14 and the handheld terminal device 16 but image data is not communicated. In the radiographic imaging system 10 according to each of the exemplary embodiments described above, because data with small volumes (the image ID and the association information) is communicated, communications may be implemented with consideration for communication conditions between the radiographic imaging device 14 and the handheld terminal device 16 (circuit capacity, the presence of effects such as noise and the like, and so forth). In imaging, with consideration for obstructing positioning of the imaging subject W and the like, communications are generally implemented by wireless rather than communications by wire. In cases of communications by wireless, there are significant concerns about crosstalk, and if data with large volumes such as image data is communicated, there may be cases of communication delays and communication failures. Moreover, in cases of communicating image data, with a view to speed, it may not be possible to use general-purpose, low-cost communication modules such as Bluetooth (registered trademark), beacon modules or the like. However, in the radiographic imaging system 10 according to each of the exemplary embodiments described above, because image data is not communicated at the location of imaging, such problems may be suppressed.

Image data is not memorized at the handheld terminal device 16 of the radiographic imaging system 10 of each of the exemplary embodiments described above. Therefore, the memory section 32 may be a memory section (memory) with a small capacity.

In a case in which a radiographic imaging device receives an order and associates image data with the order, if an imaging sequence (the order) is altered, there is a risk that delays may occur and that associations may not be easily made. If such delays are to be corrected, the provision of an operation section and display section or the like for that purpose at the radiographic imaging device is necessary. Thus, the weight of the radiographic imaging device may increase and costs may increase. In contrast, in the radiographic imaging device 14 according to each of the exemplary embodiments described above, the radiographic imaging device 14 associates image IDs and image data without receiving orders. Therefore, this problem may be inhibited.

For each of the exemplary embodiments described above, a case is described in which the radiographic imaging device 14 generates image IDs. However, image IDs may be generated by the handheld terminal device 16. An example of processing that is executed by the control section 30 of the handheld terminal device 16 if image IDs are generated at the handheld terminal device 16 is shown in FIG. 27. FIG. 27 shows a case in which the image IDs are generated at the handheld terminal device 16 according to the first exemplary embodiment. Therefore, the flow of processing is the same as in the first exemplary embodiment except for the generation of an image ID: step S107 is provided instead of step S106 of the first exemplary embodiment (see FIG. 3). In step S107, an image ID is created in addition to the association information, and the image ID is transmitted to the radiographic imaging device 14 in addition to the association information. In this case, although not shown in the drawings, the image IDs are not generated at the radiographic imaging device 14; it is sufficient for the radiographic imaging device 14 to associate an image ID received from the handheld terminal device 16 with the image data of a radiographic image and memorize the same in the memory section 24. An image ID may be transmitted to the handheld terminal device 16 after imaging of a radiographic image at the radiographic imaging device 14, or after memorization thereof in the memory section 24, and the handheld terminal device 16 may make a determination as to whether or not the image ID has been suitably associated.

Further, an image ID may be generated before imaging (for example, as in the first exemplary embodiment) or may be generated after imaging (for example, as in the second exemplary embodiment). Namely, Image IDs may be generated before and after imaging.

Thus, an image ID may be generated at either of the radiographic imaging device 14 and the handheld terminal device 16 and may be generated either of before and after imaging. However, it is preferable if the radiographic imaging device 14 generates an image ID after a completion of imaging. Consequently, image IDs may be reliably associated at the radiographic imaging device 14 with image data that has been memorized in the memory section 24.

If the radiographic imaging system 10 is equipped with a plural number of the handheld terminal devices 16, image IDs are generated at each of the handheld terminal devices 16. Therefore, it may be that matching image IDs are generated at respective handheld terminal devices 16. In this case, because matching image IDs are present in the memory section 24 of the radiographic imaging device 14, it is not possible to distinguish between the handheld terminal devices 16 that generated the image IDs. However, in a case in which image IDs are generated at the radiographic imaging device 14, the presence of matching image IDs in the memory section 24 may be prevented. In this case, if the radiographic imaging system 10 is equipped with a plural number of the radiographic imaging devices 14, the image IDs are received at the handheld terminal devices 16 from the radiographic imaging devices 14. Therefore, it is possible that matching image IDs may be present in the memory sections 32. However, it is sufficient to associate and memorize imaging device IDs with the image IDs.

If the handheld terminal device 16 generates image IDs in a case in which the radiographic imaging system 10 is equipped with a plural number of the radiographic imaging devices 14, then if image data imaged by all of the radiographic imaging devices 14 is gathered at the console 18 or the like, image IDs that are associated with the same patient ID are sequential numbers. However, in each radiographic imaging device 14, it is possible that image IDs that are present in the memory section 24 are not sequential. However, in a case in which the image IDs are generated by the radiographic imaging devices 14, the image IDs that are present in each memory section 24 may be sequential numbers.

Which of the radiographic imaging device 14 and the handheld terminal device 16 generates the image IDs may be made switchable by users. Thus, which of the radiographic imaging device 14 and the handheld terminal device 16 generates the image IDs may be switched in accordance with the requirements of users, such as a service technician or the like performing maintenance of the radiographic imaging system 10 or the like.

In each of the exemplary embodiments described above, cases are described in which the radiographic imaging system 10 is provided with one of the handheld terminal device 16, but this is not limiting. The radiographic imaging system 10 may be equipped with a plural number of the handheld terminal device 16. In this case, each handheld terminal device 16 other than a handheld terminal device 16 that is being used may be prevented from going into the effective state. Information for specifying the handheld terminal device 16 being used for imaging is, for example, a PDAID or the like, and is preferably associated with image IDs and memorized in the memory section 32.

With consideration for effects on the imaging of radiographic images, it is preferable not to communicate image data at least during the actual imaging. It is also preferable not to communicate image data during the processing routines described above for each of the above exemplary embodiments.

In each of the exemplary embodiments described above, a case is described in which image IDs and association information are communicated between the radiographic imaging device 14 and the handheld terminal device 16. However, information to be communicated between the radiographic imaging device 14 and the handheld terminal device 16 is not limited thus. If a radiographic image is to be imaged using the handheld terminal device 16, then in addition to the image ID, other information to support the imaging may be communicated. This information may include, for example, a number of radiographic images that can be imaged by the radiographic imaging device 14 (the remaining capacity of the memory section 24), calibration requirements, information on remaining capacity of a power supply of the radiographic imaging device 14 (not shown in the drawings), radiation X detection information, wireless strength (of wireless communications between the radiographic imaging device 14 and the handheld terminal device 16), and the like.

It is preferable if other information is associated and memorized with the image ID.

For example, irradiation results information, representing results of an irradiation of the radiation X from the radiation irradiation device 12 onto the radiographic imaging device 14, may be associated. Specific examples of this information representing the results include a tube current, a tube voltage, an irradiation duration, an irradiation region (an opening region of a collimator) and the like. In imaging of a radiographic image, imaging may be carried out without using a grid that is for eliminating scattering caused by transmission through the imaging subject W; virtual grid processing on the basis of characteristics of a grid that is hypothetically used may be carried out by image processing of image data of the imaged radiographic image to, similarly to a case in which a grid is provided, eliminate the effects of scattering. Amounts of scattering correspond to amounts of the irradiated radiation X. Therefore, by the association of information representing the results described above, the accuracy of virtual grid processing of the image data of an associated radiographic image may be improved.

Further, information representing whether or not imaging is carried out using a grid may be associated. In this case, a determination may be made as to whether to apply virtual grid processing to the image data of the associated radiographic image.

Information representing a user carrying out the imaging (a user ID or the like) may also be associated.

Information representing the top and bottom (head and foot) of a radiographic image may also be associated. In a case in which a user interprets the associated radiographic image, the equipment that is used for the interpretation may automatically adjust to the top and bottom (head and foot) of the radiographic image.

Information representing where an order has been accepted from (for example, if an order is received from the console 18, a console ID or the like) may also be associated. In this case, the transmission source of an order may be easily identified.

Commonly, in a case in which a radiographic image is imaged, a need may arise for an additional image (hereinafter referred to as additional imaging) in addition to the order that has been provided. In this case, if the handheld terminal device 16 is not connected with the console 18 or an external system, the handheld terminal device 16 first images the radiographic image without an order corresponding to the additional imaging having been issued. After the imaging, in a case in which the handheld terminal device 16 is connected with the console 18 or external system, the order is associated with image data of the additional radiographic image. Therefore, if imaging is carried out in a state in which an order has not been issued, as in additional imaging or the like, information representing the fact that an order has not been issued may be associated. In this case, it is simple to associate the image data of the radiographic image with the order at the console 18 or the like after the imaging.

In the fifth and sixth exemplary embodiments described above, in a case in which the radiographic imaging device 14 transmits image data of a preview image, the image data of the preview image and the image ID corresponding to the image data are transmitted to the handheld terminal device 16 at timings that are apparently the same (matching timings). However, the same may be transmitted to the handheld terminal device 16 at different timings.

In the fifth and sixth exemplary embodiments described above, the radiographic imaging device 14 generates an image ID after acquiring a radiographic image. However, the radiographic imaging device 14 may generate an image ID and transmit the image ID to the handheld terminal device 16 before the acquisition of a radiographic image (before imaging).

In the cases of the second, sixth and seventh exemplary embodiments described above, in which the radiographic imaging device 14 makes a determination as to whether the radiation X has been falsely detected, it is preferable if the number of image IDs that the radiographic imaging device 14 generates and memorizes in the memory section 24 does not differ from the number of image IDs that the handheld terminal device 16 receives from the radiographic imaging device 14 and memorizes in the memory section 32. Therefore, it is preferable if, for example, a counter or the like is provided that counts the number of image IDs generated at the radiographic imaging device 14 and memorized in the memory section 24, count values of this counter are transmitted to the handheld terminal device 16, the handheld terminal device 16 appropriately compares a received count value of the counter with the number of image IDs memorized in the memory section 32, and the handheld terminal device 16 gives a warning or the like if the values do not coincide. Further, the handheld terminal device 16 may display the count value of the counter at the display 36.

The configuration of the image IDs is not particularly limited. However, for radiographic images obtained by a pre-specified sequence of imaging, such as radiographic images imaging the same imaging subject W, divided imaging in which an imaging region corresponding to a large imaging target is divided up and imaged a plural number of times, or the like, it is preferable to include information indicating this situation in the image IDs. For example, in a case of divided imaging, the configuration of the image IDs may be the same serial number with symbols corresponding to a division sequence (as a specific example, a, b, c, etc.) appended, or the like. Thus, in a case in which radiographic images are to be joined after imaging to generate an image corresponding to a single large imaging region, the joining of the radiographic images may be facilitated.

In each of the exemplary embodiments described above, the radiographic imaging system 10 that utilizes a doctor's trolley or the like is described in detail, but this is not limiting. For example, the whole of the radiographic imaging system 10 or part of the radiographic imaging system 10 may be disposed and used outside a hospital or in the outdoors. In this case, the whole of the radiographic imaging system 10 (all the devices) may be driven by batteries.

In each of the exemplary embodiments described above, cases are described in which the respective processing programs are memorized in advance at the control section 22 and the control section 30. However, the processing programs may be acquired and memorized from an external medium, such as a compact disc read-only memory (CD-ROM), universal serial bus (USB) memory or the like, or from external equipment or the like.

In each of the exemplary embodiments described above, the radiation of the present invention is not particularly limited; X-rays, gamma rays or the like may be employed.

Configurations, operations and the like of the radiographic imaging system 10, the radiographic imaging device 14, the handheld terminal device 16, the console 18 and the like described in each of the above exemplary embodiments are examples; it will be clear that modifications are possible in accordance with circumstances within a scope not deviating from the gist of the present invention. It will also be clear that the exemplary embodiments described above may be combined.

What is claimed is:

1. A radiographic imaging system comprising:
   a radiographic imaging device that images a radiographic image of an imaging target;
   a handheld terminal device;
   a first memory section at which image information of the radiographic image and identification information that identifies the image information are associated and stored; and
   a second memory section, different from the first memory section, at which imaging target information relating to the imaging target and the identification information are associated and stored,
   wherein the identification information identifying the image information is generated at one of the radiographic imaging device or the handheld terminal device,
   wherein the radiographic imaging device associates the identification information with the image information, and stores the same at the first memory section,
   wherein, in a case in which the imaging target information and the identification information have been associated and stored at the second memory section, the handheld terminal device generates association information and transmits the association information, and
   wherein the radiographic imaging device receives the association information transmitted from the handheld terminal device.

2. The radiographic imaging system according to claim 1, wherein
   the radiographic imaging device includes:
      the first memory section;
      an imaging section that images the radiographic image;
      a first generation section that generates the identification information;
      a first control section that controls to associate the image information with the identification information generated by the first generation section, and store the same at the first memory section;
      a first transmission section that transmits the identification information to the handheld terminal device; and
      a first reception section that receives the association information from the handheld terminal device, and
   the handheld terminal device includes:
      the second memory section;
      a second reception section that receives the identification information from the radiographic imaging device;
      an acquisition section that acquires the imaging target information;
      a second control section that controls to associate the imaging target information acquired by the acquisition section with the identification information received by the second reception section, and store the same at the second memory section;
      a second generation section that generates the association information in a case in which the imaging target information and the identification information have been associated and stored by the second control section; and
      a second transmission section that transmits the association information generated by the second generation section to the radiographic imaging device.

3. The radiographic imaging system according to claim 1, wherein the handheld terminal device permits imaging of the radiographic image at the radiographic imaging device in a case in which the association information has been generated.

4. The radiographic imaging system according to claim 2, wherein:
   the radiographic imaging device generates the identification information via the first generation section, and transmits the identification information via the first transmission section before imaging of the radiographic image by the imaging section; and
   after the transmission of the identification information, the first control section permits the imaging of the radiographic image at the imaging section in a case in which the first reception section has received the association information.

5. The radiographic imaging system according to claim 2, wherein:
   the radiographic imaging device transmits the identification information via the first transmission section after imaging of the radiographic image by the imaging section; and
   after the transmission of the identification information, the first control section permits imaging of a subsequent radiographic image at the imaging section in a case in which the first reception section has received the association information.

6. The radiographic imaging system according to claim 5, wherein the identification information that identifies the image information acquired by the imaging is generated by the first generation section after the imaging of the radiographic image by the imaging section.

7. The radiographic imaging system according to claim 2, wherein the handheld terminal device further includes:
   an operation section that is configured to receive the imaging target information from a user; and
   a first acceptance section that, in a case in which the identification information has been received by the second reception section, accepts the imaging target information received from the user with the operation section for the received identification information, and wherein the acquisition section acquires the imaging target information accepted by the first acceptance section.

8. The radiographic imaging system according to claim 2, wherein:
   the handheld terminal device further includes a first display section that displays the identification information received by the second reception section; and
   the second control section controls to display the identification information received by the second reception section at the first display section.

9. The radiographic imaging system according to claim 2, wherein the handheld terminal device further includes:
   a second display section that displays the imaging target information acquired by the acquisition section; and
   a second acceptance section that accepts an amendment received from the user for the imaging target information displayed at the second display section, and
   wherein the second control section controls to display the imaging target information acquired by the acquisition section at the second display section, and controls to associate imaging target information that has been corrected in accordance with an amendment accepted by the second acceptance section with the identification information and to store the same at the second memory section.

10. The radiographic imaging system according to claim 2, wherein:
    the radiographic imaging device comprises a plurality of radiographic imaging devices; and
    the second control section of the handheld terminal device controls to associate the identification information transmitted by the first transmission section of the radiographic imaging device and received by the second reception section with information representing the radiographic imaging device that is the source of the transmission of the identification information, and to store the same at the second memory section.

11. The radiographic imaging system according to claim 2, wherein:
    the radiographic imaging device comprises a plurality of radiographic imaging devices;
    the handheld terminal device includes a designation section at which at least one radiographic imaging device among the plurality of radiographic imaging devices is designated; and
    the second control section controls to associate information representing the radiographic imaging device that has been designated at the designation section with the identification information transmitted by the first transmission section of the radiographic imaging device and received by the second reception section, and to store the same at the second memory section.

12. The radiographic imaging system according to claim 11, wherein, if the second reception section receives the identification information from one of the radiographic imaging devices that is different from the radiographic imaging device designated by the designation section, the second control section of the handheld terminal device controls to associate information representing the radiographic imaging device that is the source of the transmission of the identification information with the identification information, and to store the same at the second memory section.

13. The radiographic imaging system according to claim 2, wherein the first memory section associates and stores a plurality of the image information with a plurality of the identification information generated by the first generation section.

14. The radiographic imaging system according to claim 2, further comprising a control device including:
    a third memory section at which the image information and imaging target information associated with the same identification information are associated and stored;
    a third reception section that receives the image information and the corresponding identification information from the radiographic imaging device, and receives the imaging target information and the identification information associated with the imaging target information from the handheld terminal device; and
    a third control section that controls imaging of the radiographic image by the radiographic imaging device, and controls to associate the image information and the imaging target information associated with the same imaging identification information, and to store the same at the third memory section.

15. The radiographic imaging system according to claim 2, wherein the handheld terminal device further comprises a fourth control section that controls the imaging of the radiographic image by the radiographic imaging section.

16. The radiographic imaging system according to claim 2, wherein the handheld terminal device further comprises:
    a third memory section at which the image information and imaging target information associated with the same identification information are associated and stored;
    a third reception section that receives the image information corresponding to the identification information received from the radiographic imaging device by the second reception section; and
    a third control section that controls imaging of the radiographic image by the radiographic imaging device, and controls to associate the image information and imaging target information associated with the same identification information, and to store the same at the third memory section.

17. The radiographic imaging system according to claim 2, wherein the radiographic imaging device and the handheld terminal device communicate by at least one of wireless communications by electromagnetic waves or optical communications by light.

18. The radiographic imaging system according to claim 2, wherein the radiographic imaging device further includes:
    a third generation section that generates a preview image from image data of the radiographic image; and
    a third transmission section that transmits image information of the preview image generated by the third generation section to the handheld terminal device, and the handheld terminal device further includes:

a fourth reception section that receives the preview image from the radiographic imaging device; and a third display section that displays the preview image received by the fourth reception section.

19. The radiographic imaging system according to claim 1, wherein the radiographic imaging device includes:

the first memory section;

an imaging section that includes the function for imaging the radiographic image;

a first control section that controls to associate the image information with the identification information, and to store the same at the first memory section;

a first transmission section that transmits the identification information to the handheld terminal device; and a first reception section that receives the association information and the identification information from the handheld terminal device, and the handheld terminal device includes:

the second memory section;

an acquisition section that acquires the imaging target information;

a first generation section that generates the identification information;

a second control section that controls to associate the imaging target information acquired by the acquisition section with the identification information, and to store the same at the second memory section;

a second generation section that generates the association information in a case in which the imaging target information and the identification information have been associated and stored by the second control section; and a second transmission section that transmits the association information generated by the second generation section to the radiographic imaging device.

20. A radiographic imaging device comprising:

an imaging section that images a radiographic image of an imaging target;

a generation section that generates identification information that identifies image information of the radiographic image;

a memory section at which the image information and the identification information generated by the generation section are associated and stored;

a control section that controls to associate the image information with the identification information generated by the generation section, and to store the same at the memory section;

a transmission section that transmits the identification information; and a reception section that receives association information from a handheld terminal device, the association information indicating that imaging target information relating to the imaging target and the identification information have been associated and stored.

21. A handheld terminal device comprising:

a reception section that receives, from a radiographic imaging device, identification information that identifies image information of a radiographic image of an imaging target imaged by the radiographic imaging device;

an acquisition section that acquires imaging target information relating to the imaging target;

a memory section at which the imaging target information acquired by the acquisition section and the identification information received by the reception section are associated and stored, a control section that controls to associate the imaging target information acquired by the acquisition section with the identification information received by the reception section, and to store the same at the memory section; and a transmission section that transmits association information to the radiographic imaging device in a case in which the imaging target information and the identification information have been associated and stored by the control section.

22. A radiographic imaging method according to a radiographic imaging system that includes, a radiographic imaging device that images a radiographic image of an imaging target, a handheld terminal device, a first memory section at which image information of the radiographic image and identification information that identifies the image information are associated and stored, and a second memory section, different from the first memory section, at which imaging target information relating to the imaging target and the identification information are associated and stored, the radiographic imaging method comprising:

generating, by the radiographic imaging device or the handheld terminal device, the identification information that identifies the image information of the radiographic image;

associating, by the radiographic imaging device, the identification information with the image information, and storing the same at the first memory section;

generating, by the handheld terminal device, association information and transmitting the association information to outside the handheld terminal device, in a case in which the imaging target information relating to the imaging target and the identification information have been associated and stored at the second memory section that is different from the first memory section; and receiving, by the radiographic imaging device, the association information transmitted from the handheld terminal device.

\* \* \* \* \*